(12) United States Patent
Bishop et al.

(10) Patent No.: US 7,470,769 B2
(45) Date of Patent: Dec. 30, 2008

(54) EPIDERMAL GROWTH FACTOR RECEPTOR ANTAGONISTS AND METHODS OF USE

(75) Inventors: Jeffrey S. Bishop, Spring, TX (US); A. Katrina Loomis, Houston, TX (US); Daniel J. Monticello, The Woodlands, TX (US); Philip T. Pienkos, The Woodlands, TX (US)

(73) Assignee: Molecular Logix, Inc., The Woodlands, TX (US)

( * ) Notice: Subject to any disclaimer, the term of this patent is extended or adjusted under 35 U.S.C. 154(b) by 96 days.

(21) Appl. No.: 11/172,610

(22) Filed: Jun. 30, 2005

(65) Prior Publication Data

US 2006/0014690 A1    Jan. 19, 2006

Related U.S. Application Data

(60) Provisional application No. 60/643,082, filed on Jan. 11, 2005, provisional application No. 60/584,471, filed on Jun. 30, 2004.

(51) Int. Cl.
*C07K 14/475* (2006.01)
*C07K 14/485* (2006.01)
*C07K 14/495* (2006.01)

(52) U.S. Cl. .................. 530/300; 530/388.24; 530/399

(58) Field of Classification Search ........................ None
See application file for complete search history.

(56) References Cited

U.S. PATENT DOCUMENTS 5,102,789 A    4/1992 Siegel et al.
2005/0032162 A1    2/2005 Coco et al.

OTHER PUBLICATIONS

Mendelsohn et al. Oncogene. 2000; 19: 6550-65.*
Mendolsohn. Endocr Rel. Cancers. 2001; 8: 3-9.*
Hommel et al. Biochemistry. 1991, 30: 8891-8898.*
Shiah et al. JBC. 1992; 267; 33: 24034-24040.*
Feild et al. The Biochemical Journal. 1992: 283: 91-98.*
Rajput et al. Cancer Res. 2007; 67: 665-673.*
Wells, 1990, Biochemistry 29:8509-8517.*
Ngo et al., 1994, The Protein Folding Problem and Tertiary Structure Prediction, pp. 492-495.*
Bork, 2000, Genome Research 10:398-400.*
Skolnick et al., 2000, Trends in Biotech. 18(1):34-39.*
Doerks et al., 1998, Trends in Genetics 14:248-250.*
Smith et al., 1997, Nature Biotechnology 15: 1222-1223.*
Brenner, 1999, Trends in Genetics 15:132-133.*
Bork et al., 1996, Trends in Genetics 12:425-427.*
Defeo-Jones et al. Mol Cell Bio. 1989; 9: 4083-4086.*
U.S. Appl. No. 11/172,611, filed Jun. 30, 2005, Philip T. Pienkos, et al.
Wells, James A., "Additivity of Mutational Effects in Proteins," *Biochemistry*, 29(37): 8509-8517 (1990).
Bowie, James U., "Deciphering the Message in Protein Sequences: Tolerance to Amino Acid Substitutions," *Science*, 247: 1306-1310 (1990).
Coco, Wayne M., et al., "Growth Factor Engineering by Degenerate Homoduplex Gene Family Recombination," *Nature Biotechnology*, 20: 1246-1250 (2002).
Ben-Bassat, H. and Klein, B.Y., "Inhibitors of Tyrosine Kinases in the Treatment of Psoriasis," *Current Pharmaceutical Design*, 6: 933-942 (2000).
Arteaga, Carlos L., "Epidermal Growth Factor Receptor Dependence in Human Tumors: More Than Just Expression?" *The Oncologist*, 7(Suppl. 4): 31-39 (2002).
Ogiso, Hideo, et al., "Crystal Structure of the Complex of Human Epidermal Growth Factor and Receptor Extracellular Domains," *Cell*, 110: 775-787 (2002).
Engler, David A., et al., "Human Epidermal Growth Factor. Distinct Roles of Tyrosine 37 and Arginine 41 in Receptor Binding as Determined by Site-Directed Mutagenesis and Nuclear Magnetic Resonance Spectroscopy," *FEBS Letters*, 271(1,2): 47-50 (1990).

* cited by examiner

*Primary Examiner*—Elizabeth C. Kemmerer
*Assistant Examiner*—Christina Borgeest
(74) *Attorney, Agent, or Firm*—Darlene A. Vanstone; Carolyn S. Elmore; Elmore Patent Law Group, P.C.

(57) ABSTRACT

The present invention features epidermal growth factor receptor (EGFR) antagonists. These EGFR antagonists are polypeptide variants of ligands of EGFR. The EGFR ligand polypeptide variants of the invention possess EGFR antagonistic properties and can inhibit at least one EGFR-mediated biological activity such as inhibition of the receptor's kinase activation activity and subsequently, cell proliferation. Such polypeptide variants, and nucleic acids encoding these polypeptide variants can be used therapeutically in situations in which inhibition of EGFR activity is indicated.

11 Claims, 20 Drawing Sheets

US 7,470,769 B2

EPIDERMAL GROWTH FACTOR RECEPTOR ANTAGONISTS AND METHODS OF USE

RELATED APPLICATIONS

This application claims the benefit of U.S. Provisional Application No. 60/584,471, filed on Jun. 30, 2004 and U.S. Provisional Application No. 60/643,082, filed on Jan. 11, 2005, the contents of which are incorporated herein by reference.

GOVERNMENT SUPPORT

The Invention was supported, in whole, or in part, by National Cancer Institute Grant Number R43 CA095930-02. The Government has certain rights in the invention.

BACKGROUND OF THE INVENTION

Epidermal growth factor (EGF) is a 53 amino acid cytokine which is proteolytically cleaved from a large integral membrane protein precursor. EGF plays an important role in the growth control of mammalian cells. The amino acid and nucleotide sequences of human EGF (hEGF) are, for example, disclosed in Hollenberg, "Epidermal Growth Factor-Urogastrone, A Polypeptide Acquiring Hormonal States"; eds., Academic Press, Inc., New York (1979), pp. 69-110; or Urdea et al., Proc. Natl. Acad. Sci. USA, 80:7461 (1983). The amino acid sequence of hEGF is also disclosed in U.S. Pat. No. 5,102,789 and copending U.S. patent application Ser. No. 10/820,640 both of which are incorporated herein by reference in their entirety.

Epidermal growth factor receptor (EGFR) is a well known example of receptor tyrosine kinases. Interaction of EGFR with its cognate ligand, EGF, or with structurally related ligands (e.g. tissue growth factor α), leads to dimerization of EGFR and activation of the EGFR kinase domain. This initiates a signaling cascade, leading to cell division. Overexpression of the gene coding for the EGFR has been implicated in a number of cancers including breast, ovarian, and head and neck cancer. Molecules that target EGFR by inhibiting its kinase activity or by interfering with the binding of EGF to EGFR have been shown to inhibit cell proliferation and have been developed as anticancer therapeutics, for example, Iressa® (gefitinib), a tyrosine kinase inhibitor and Erbitux™ (cetuximab), an EGFR-specific monoclonal antibody. Although these therapeutics have been shown to be effective in some cases, there is still a need for novel therapies for EGFR-related cancers.

SUMMARY OF THE INVENTION

The present invention features EGFR antagonists. By "EGFR antagonist" is meant any molecule that inhibits, suppresses or causes the cessation of at least one EGFR-mediated biological activity, e.g. by reducing, interfering with, blocking, or otherwise preventing the interaction or binding of a native or active EFGR ligand to EGFR. These EGFR antagonists are EGFR ligand polypeptide variants. Preferred ligand variants are polypeptide molecules that are capable of blocking or interrupting at least one biological activity of EGFR, for example, reducing or inhibiting EGFR kinase activation, signaling, regulation, dimerization, or EGFR-regulated cell proliferation. Preferred ligand variants of the invention are EGF polypeptide variants capable of selectively inhibiting at least one EGFR-mediated biological activity. Such polypeptide variants, and nucleic acids encoding these polypeptide variants, can be used therapeutically in situations in which inhibition of EGFR biological activity is indicated. The term "polypeptide" is used herein as a generic term to refer to native protein, fragments, homologs or analogs of a relevant polypeptide sequence.

The present invention results from the unexpected discovery that an EGFR ligand (e.g., EGF) polypeptide variant that has one or more mutations that prevent, banish or abrogate binding of the peptide to Domain III of the EGFR and, optionally, a mutation that binds, preferably tightly, to Domain I of the EGFR can result in good to excellent EGFR antagonists having therapeutic properties. As such, the invention relates to EGFR antagonists having a polypeptide sequence substantially similar to EGF (or other EGFR ligand) characterized by at least one amino acid substitution, deletion or insertion that prevents the antagonist from binding Domain III of EGFR and, optionally at least one amino acid substitution, deletion or insertion that results in antagonist binding to Domain I of EGFR, preferably tight binding. An example of tight binding includes the formation of an ionic, covalent, hydrophobic, electrostatic or hydrogen bonds between one or more amino acids of the antagonist and the receptor. Binding can be considered "tight" if the antagonist is not substantially displaced from EGFR by EGF, e.g., in an in vitro assay such as an assay described herein. The antagonist is not substantially displaced if at least 50%, preferably at least 70%, more preferably at least about 90%, such as 100%, of the antagonist remains bound to EGFR in an assay described herein. The domains of EGFR, and similar receptors, are known and are described in Ogiso et al., *Cell,* 110:775-787 (2002), which is incorporated herein by reference.

In one aspect, the present invention features an epidermal growth factor (EGF) polypeptide variant having at least one amino acid substitution at glycine of position 39 (G39 or Gly 39) of the wild-type human EGF (hEGF) and having EGFR antagonist activity and, optionally, at valine of position 35 (V35 or Val 35). Glycine is preferably substituted with leucine (G39L) and/or valine is preferably substituted with glutamic acid (V35E).

In another aspect, the present invention features an epidermal growth factor (EGF) polypeptide variant having at least one amino acid substitution at glycine of position 18 (G18 or Gly 18) of the wild-type EGF, preferably wild-type human EGF, and having EGFR antagonist and/or inhibitory activity. In an another aspect, the present invention features an epidermal growth factor (EGF) polypeptide variant having at least one amino acid substitution at glycine of position 39 (G39 or Gly 39) of the wild-type human EGF and having EGFR antagonist activity.

The present invention also features a method of treating a condition characterized by EGFR over-expression in a patient, comprising administering to the patient a therapeutically effective amount of a pharmaceutical composition comprising at least one polypeptide variant of the invention.

BRIEF DESCRIPTION OF THE DRAWINGS

FIG. 1 is a graph of EGFR binding data for hEGF, the G39L variant and the V35EG39L variant.

FIG. 2 is a graph of an EGFR kinase assay with hEGF, the G39L variant and the V35EG39L variant, showing inhibition with the G39L mutations.

FIG. 3 is a graph of stimulation of cell proliferation with hEGF, the G39L variant and the V35EG39L variant.

FIG. 4 is a graph showing inhibition of hEGF-stimulated cell proliferation by the G39L variant.

FIG. 5 is a graph showing inhibition of hEGF-stimulated cell proliferation by the V35EG39L variant.

DETAILED DESCRIPTION OF THE INVENTION

Figure 1:
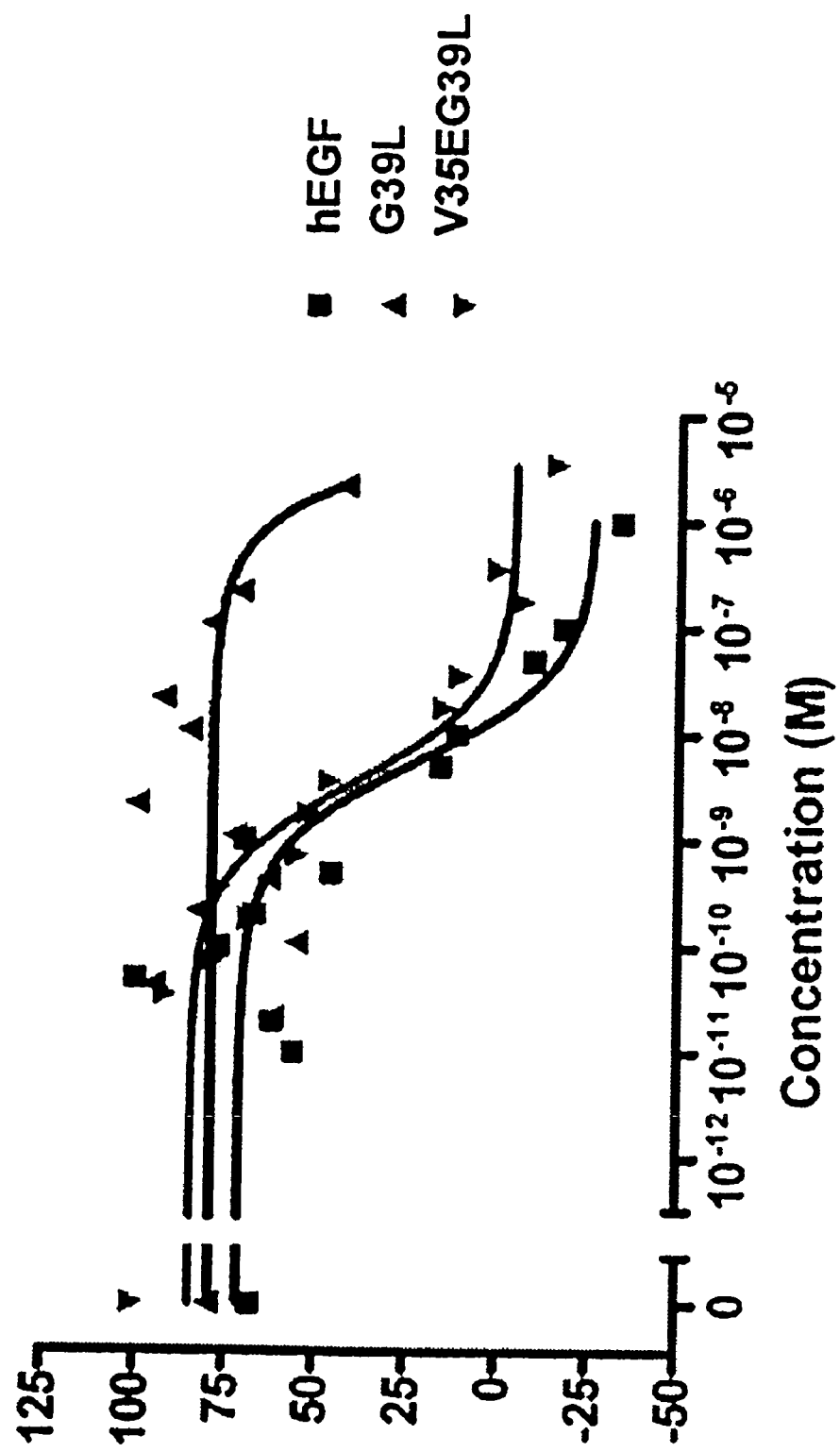
Figure 2:
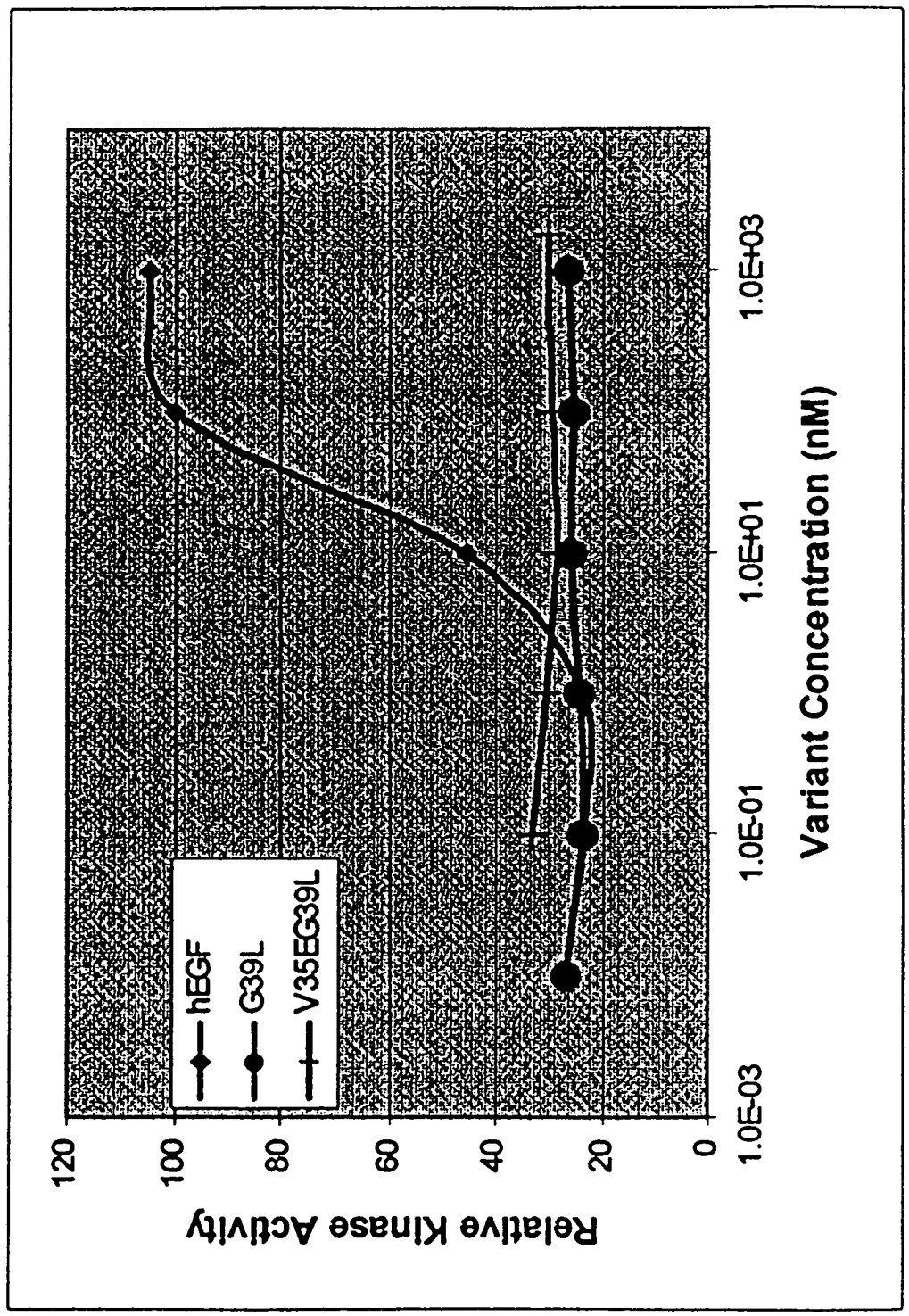
Figure 3:
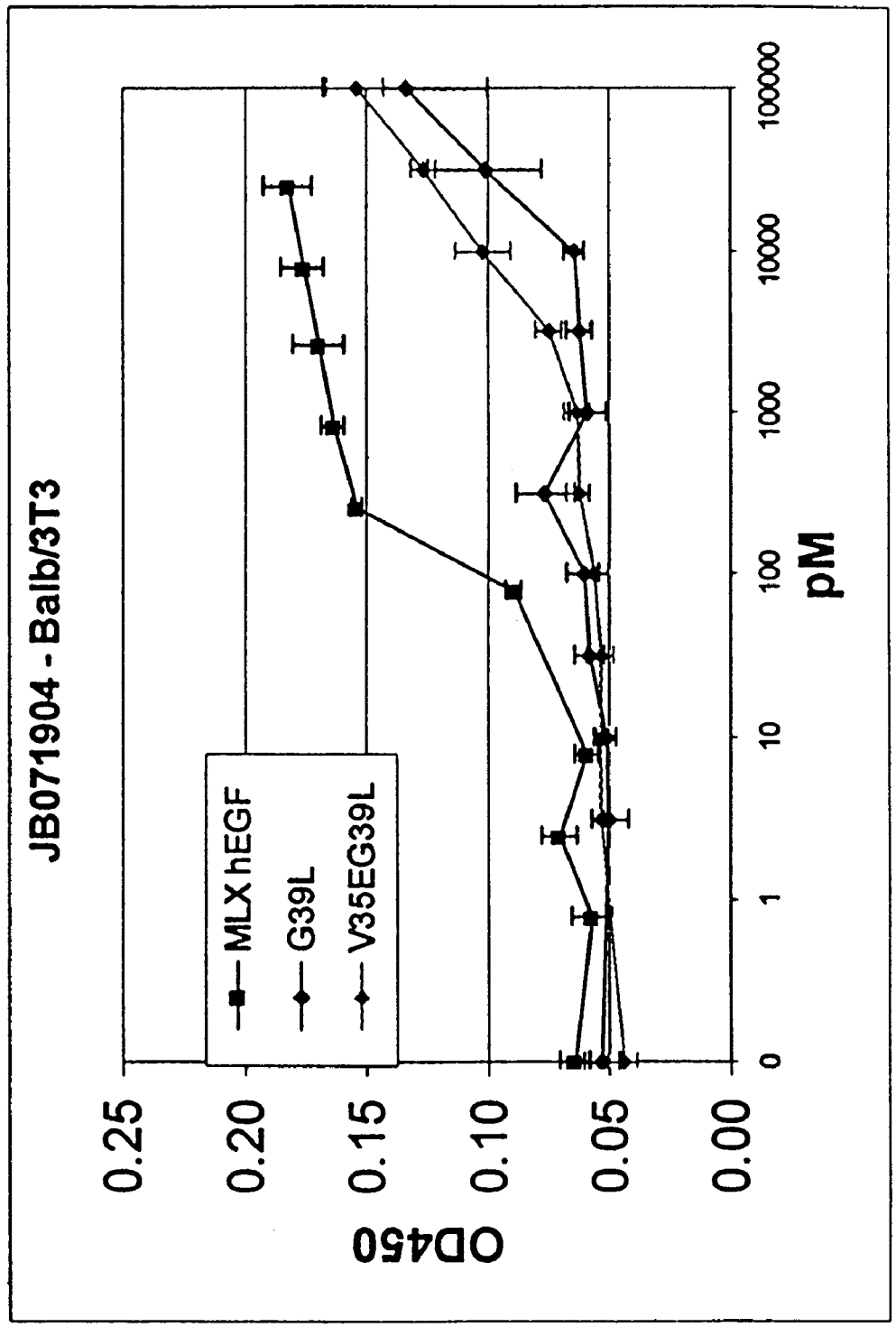
Figure 4:
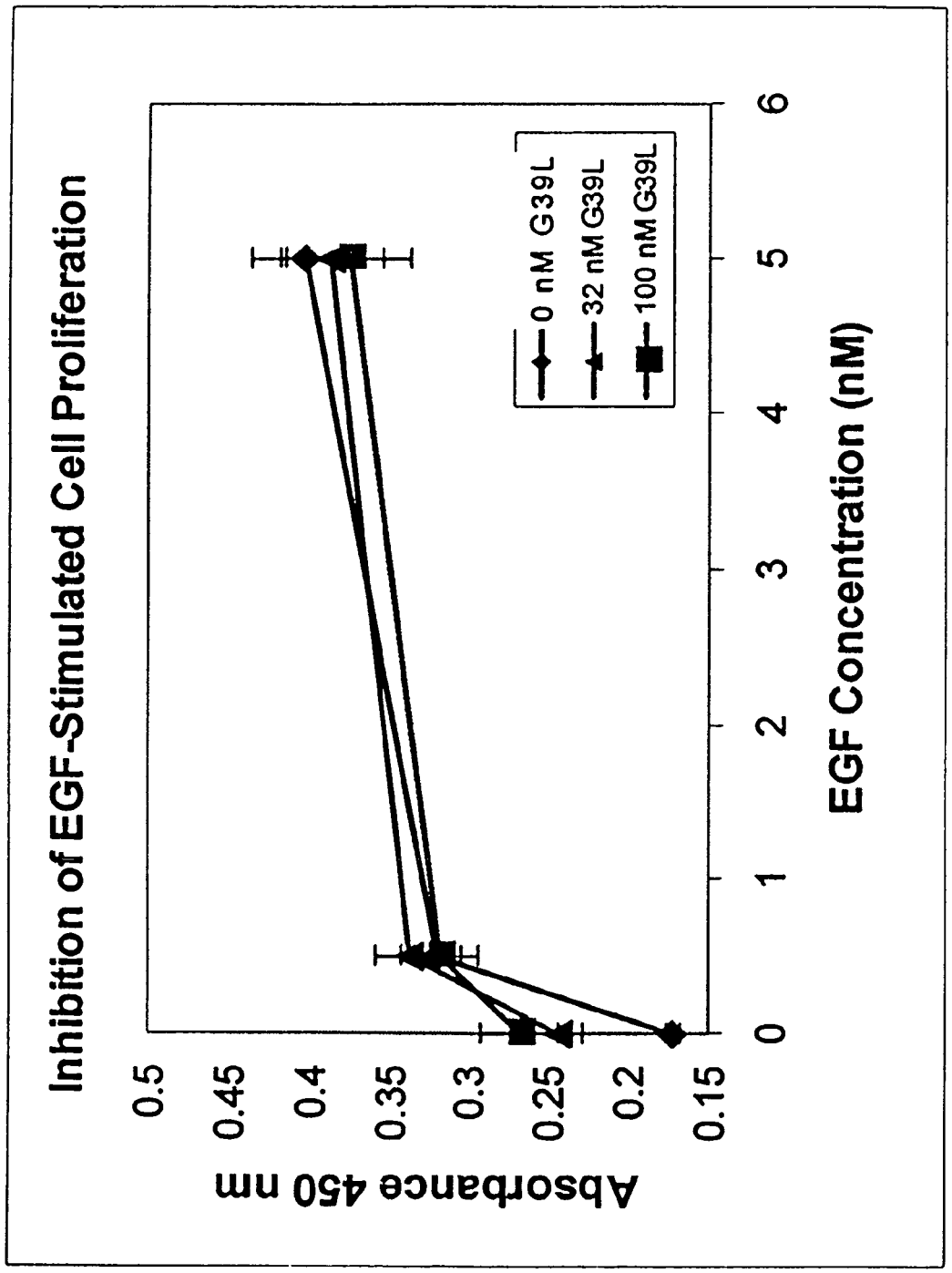
Figure 5:
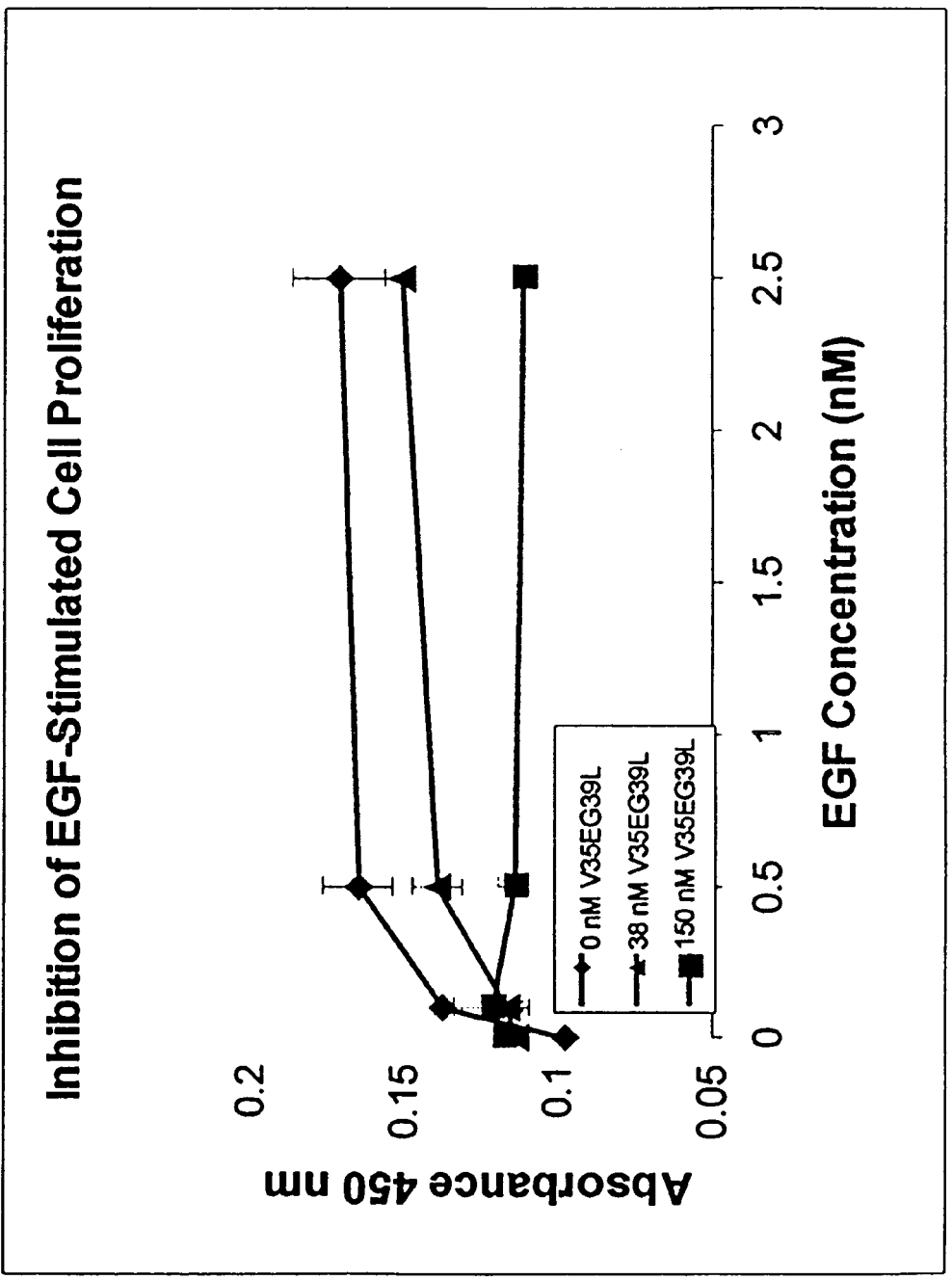
Figure 6:
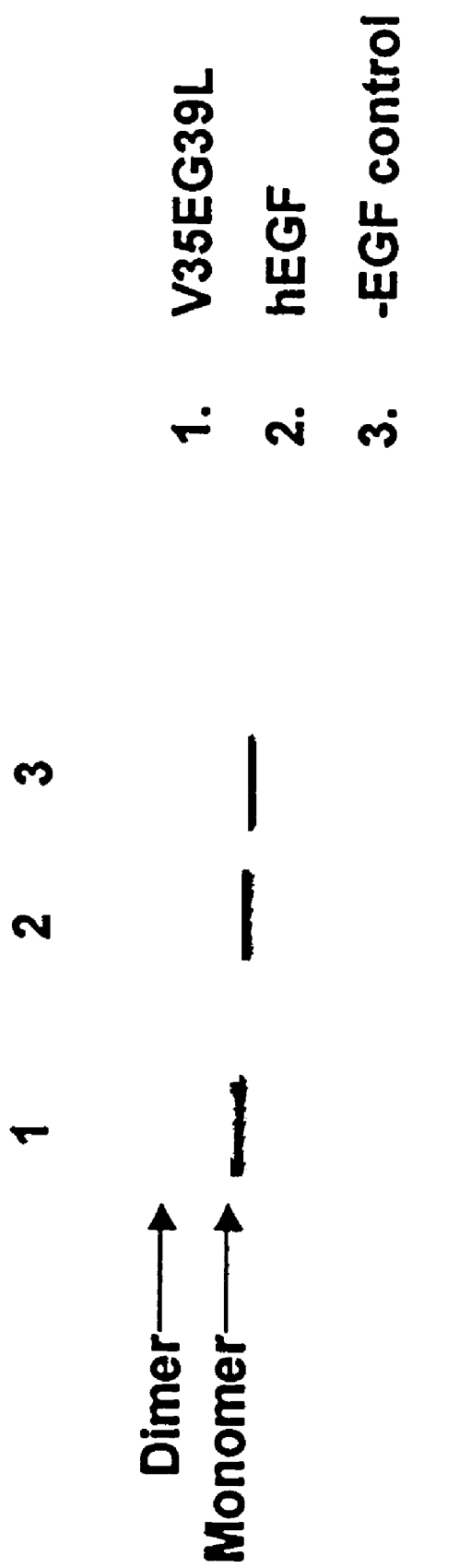
FIG. 6 illustrates that V35EG39L does not trigger EGFR dimerization.
Figure 7:
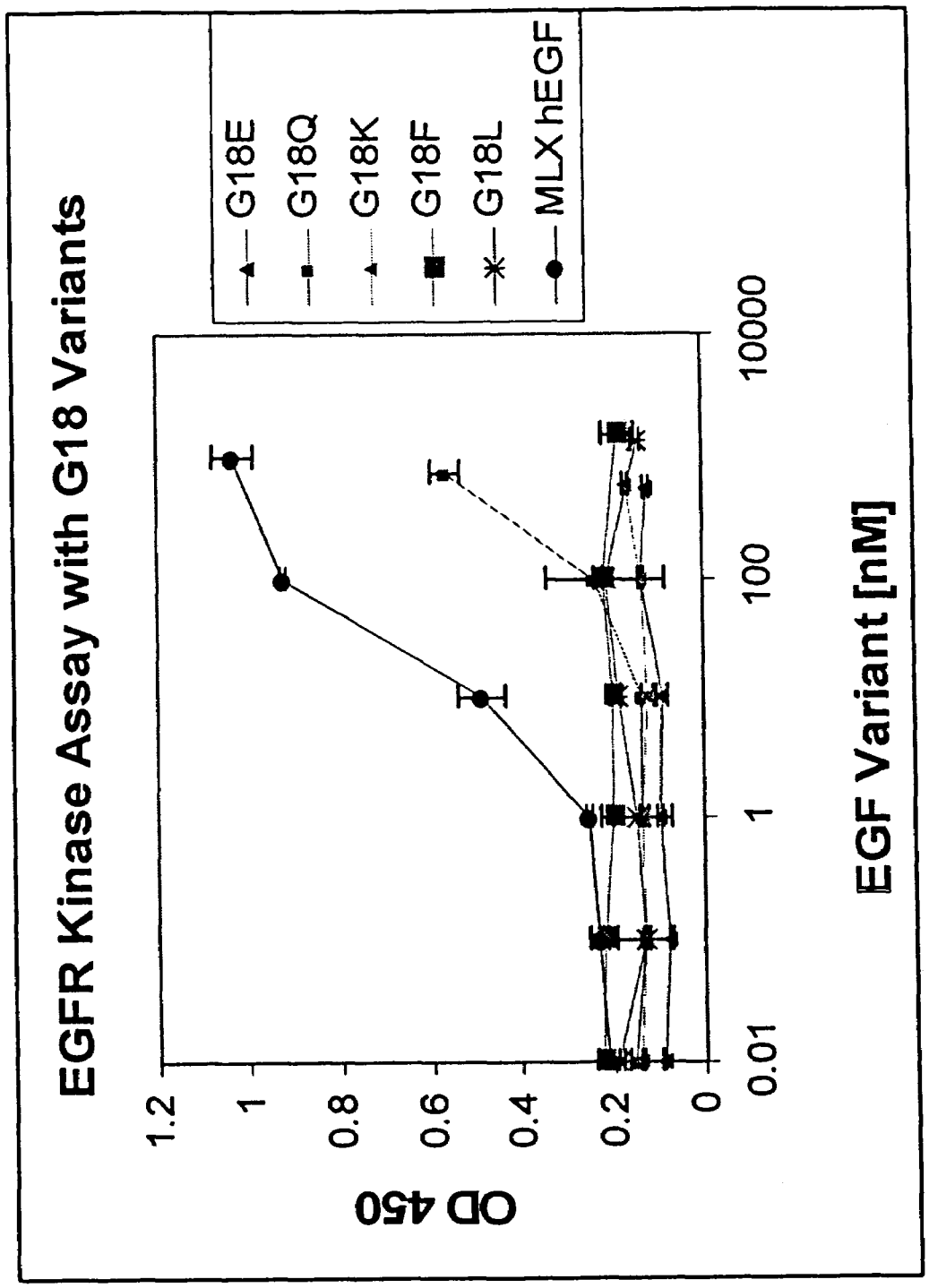
FIG. 7 is a graph of an EGFR kinase assay with EFG G18 variants.
Figure 8:
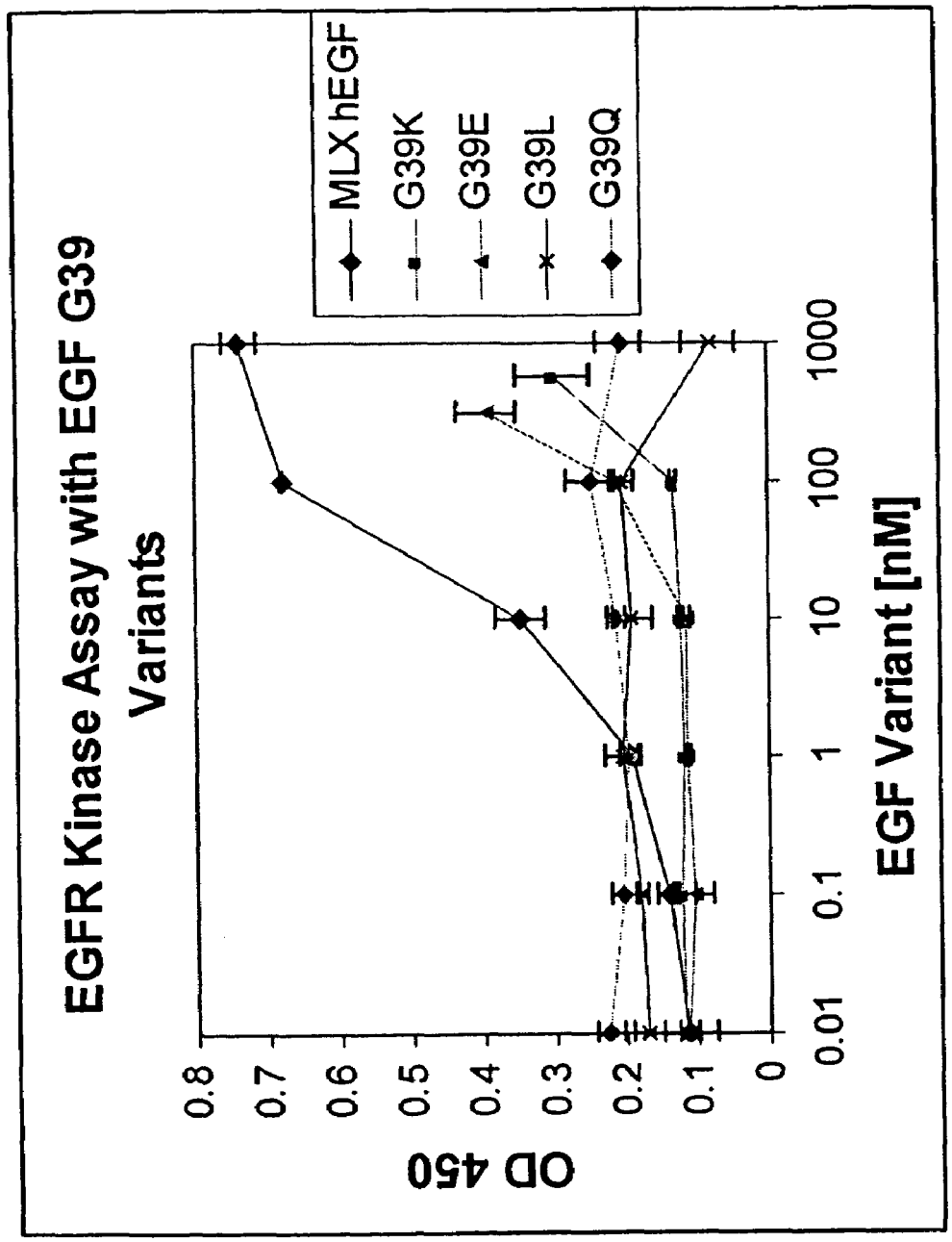
FIG. 8 is a graph of an EGFR kinase assay with EFG G39 variants
Figure 9:
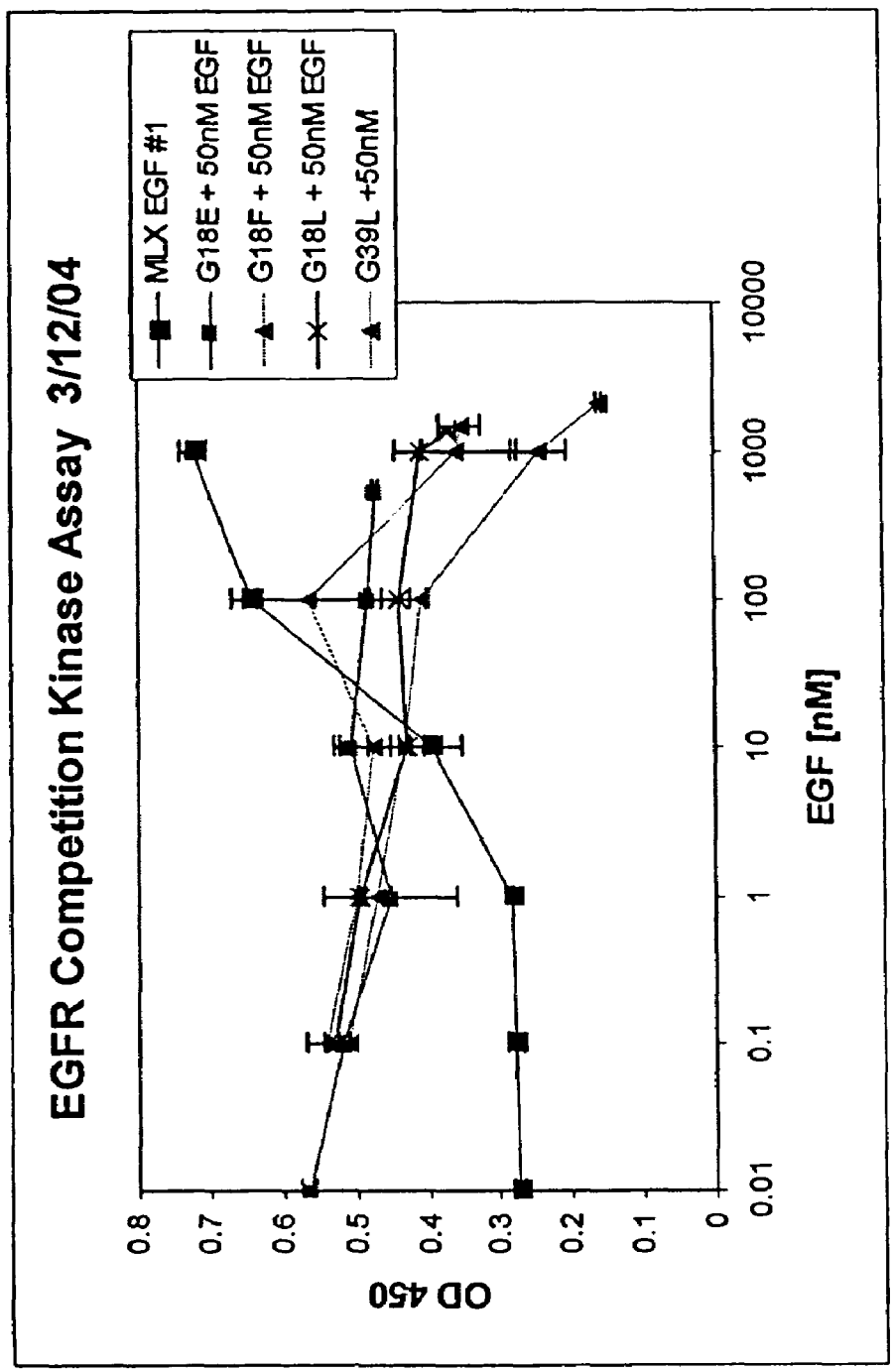
FIG. 9 is a graph of an EGFR kinase competition assay with G18 and G39 variants.
Figure 10:
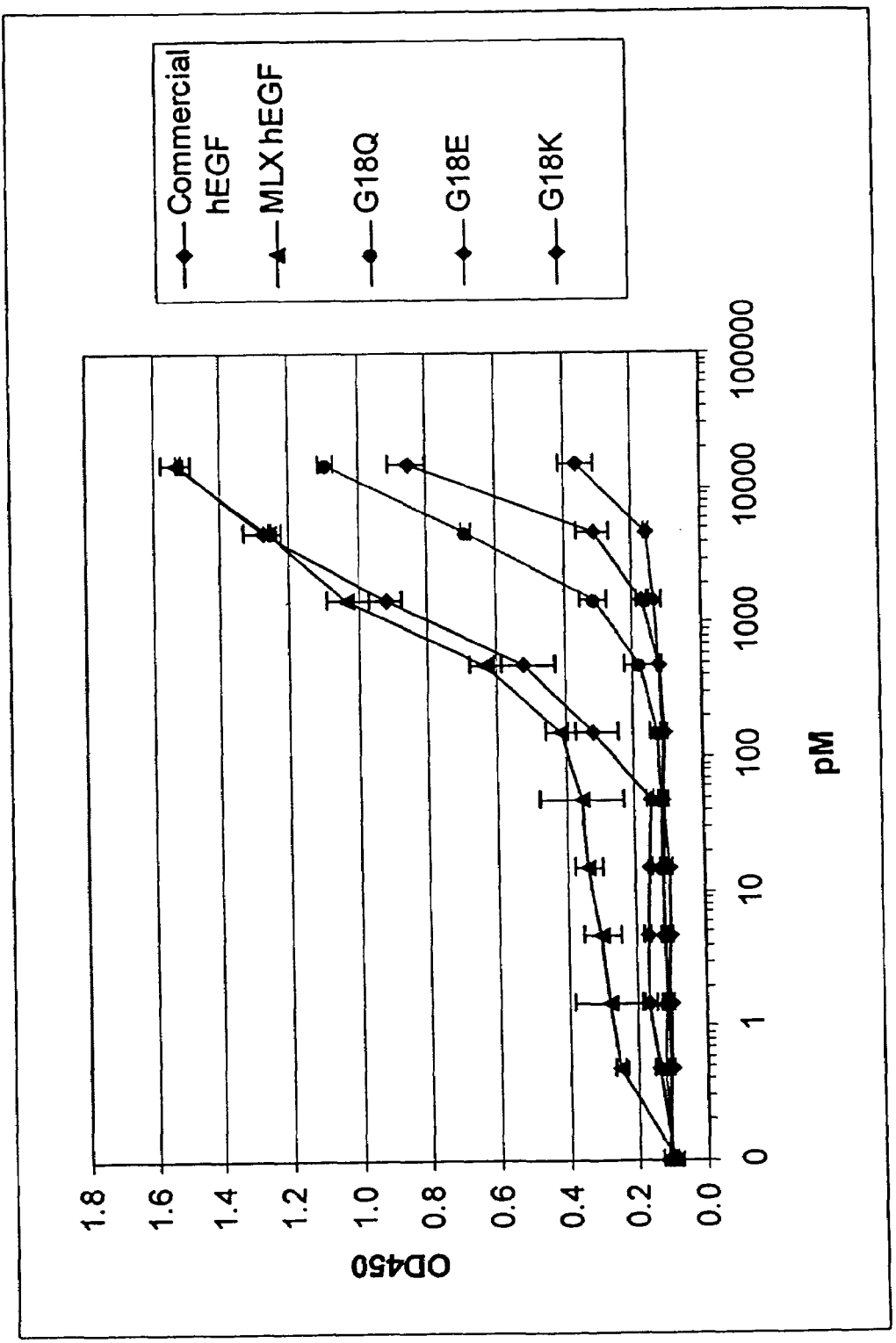
FIG. 10 is a graph showing the effect of G18E, G18K and G18Q on HER5 cell proliferation (measured as the conversion of WST-1 (4-[3-(4-iodophenyl)-2-(4-nitrophenyl)-2H-5-tetrazolio]-1,3-benzene disulfonate), to a yellow-orange, water soluble formazan by the mitochondrial dehydrogenases of viable cells which is followed by changes in the absorbance of light at 450 nm (OD 450)).
Figure 11:
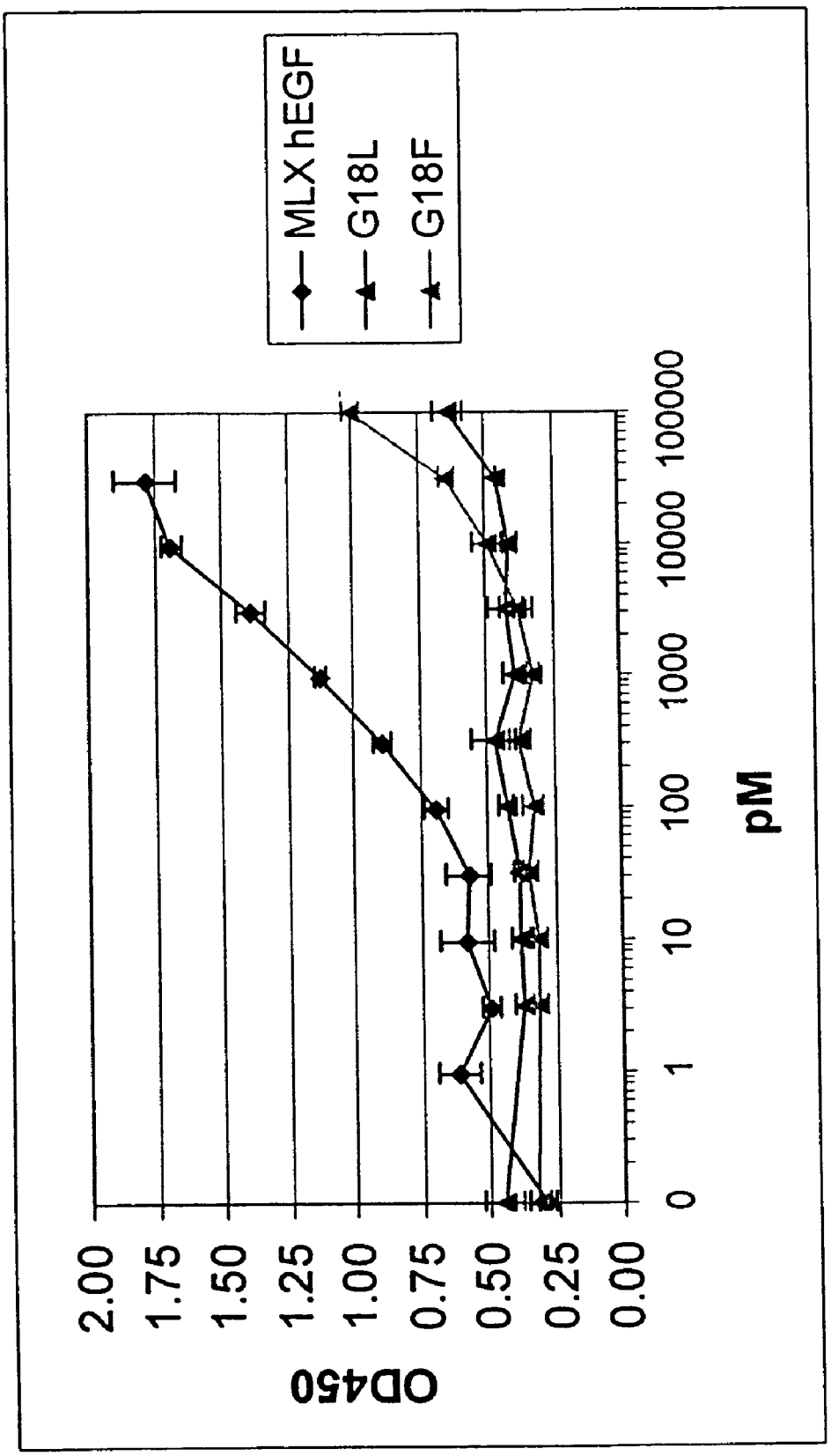
FIG. 11 is a graph showing the effect of G18F and G18L on HER5 cell proliferation (measured as the conversion of WST-1).
Figure 12:
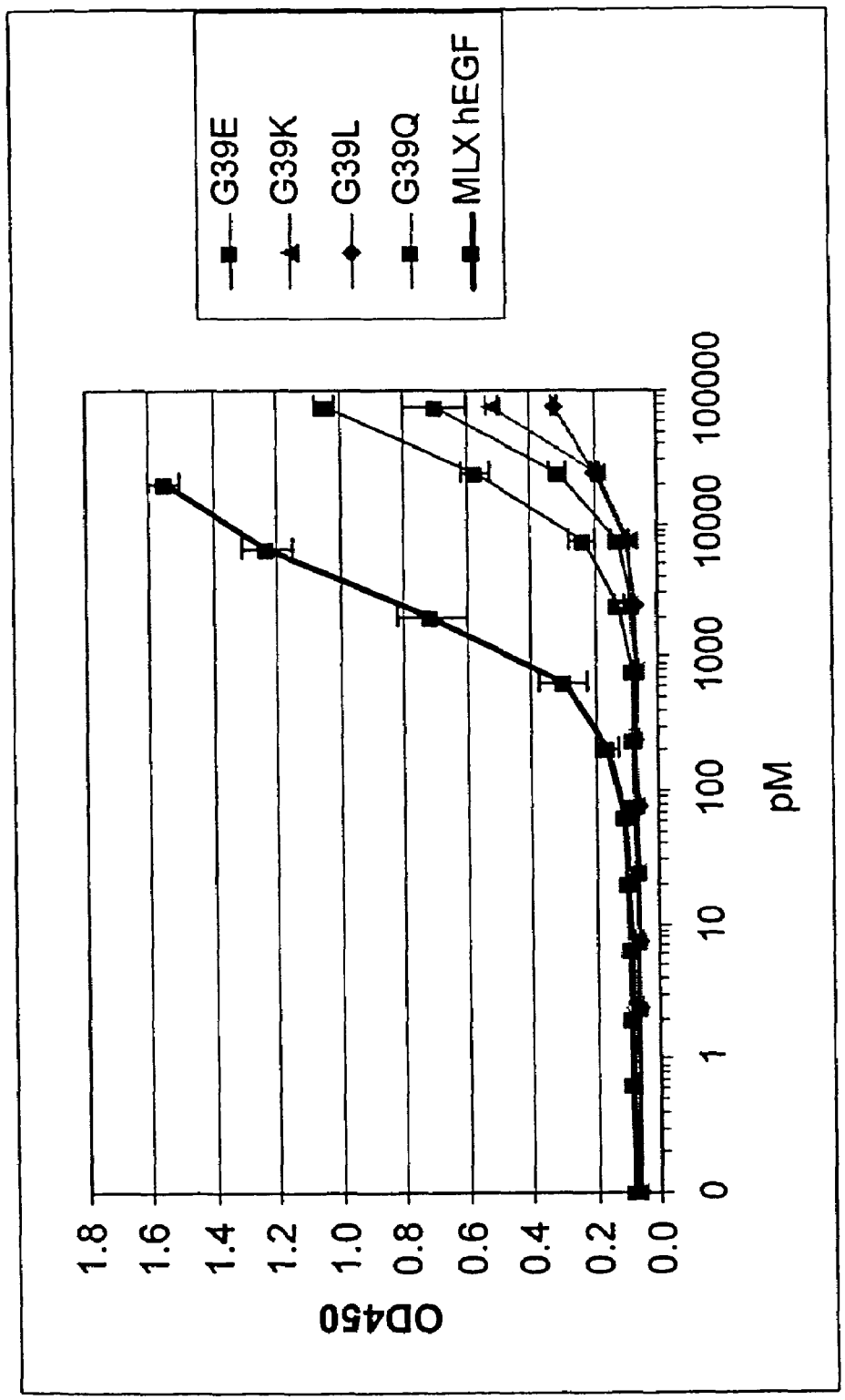
FIG. 12 is a graph showing the effect of G39 series mutants on HER 5 cell proliferation (measured as the conversion of WST-1).
Figure 13:
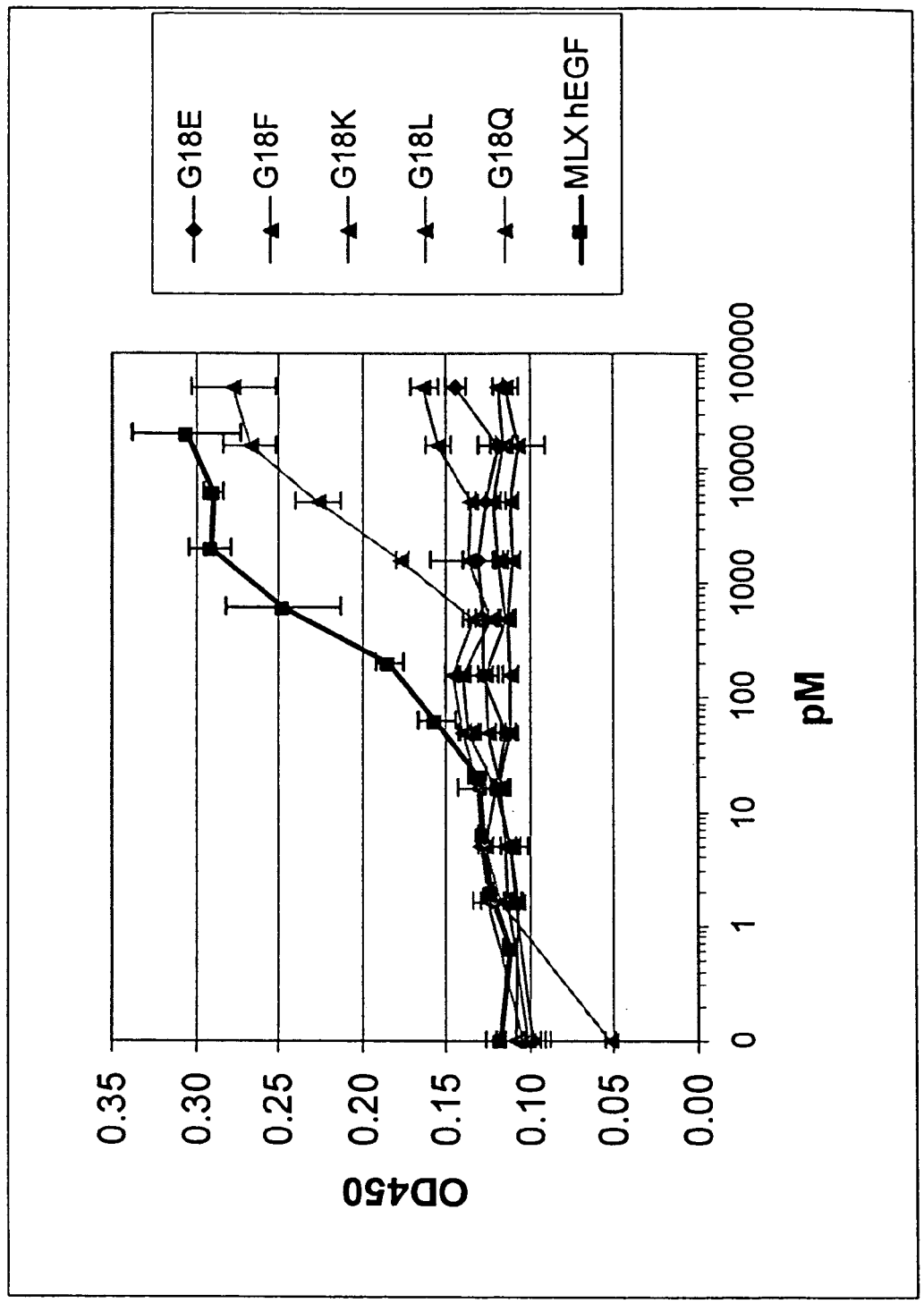
FIG. 13 is a graph showing the effect of G18 series mutants on BALB/3T3 cell proliferation (measured as the conversion of WST-1).
Figure 14:
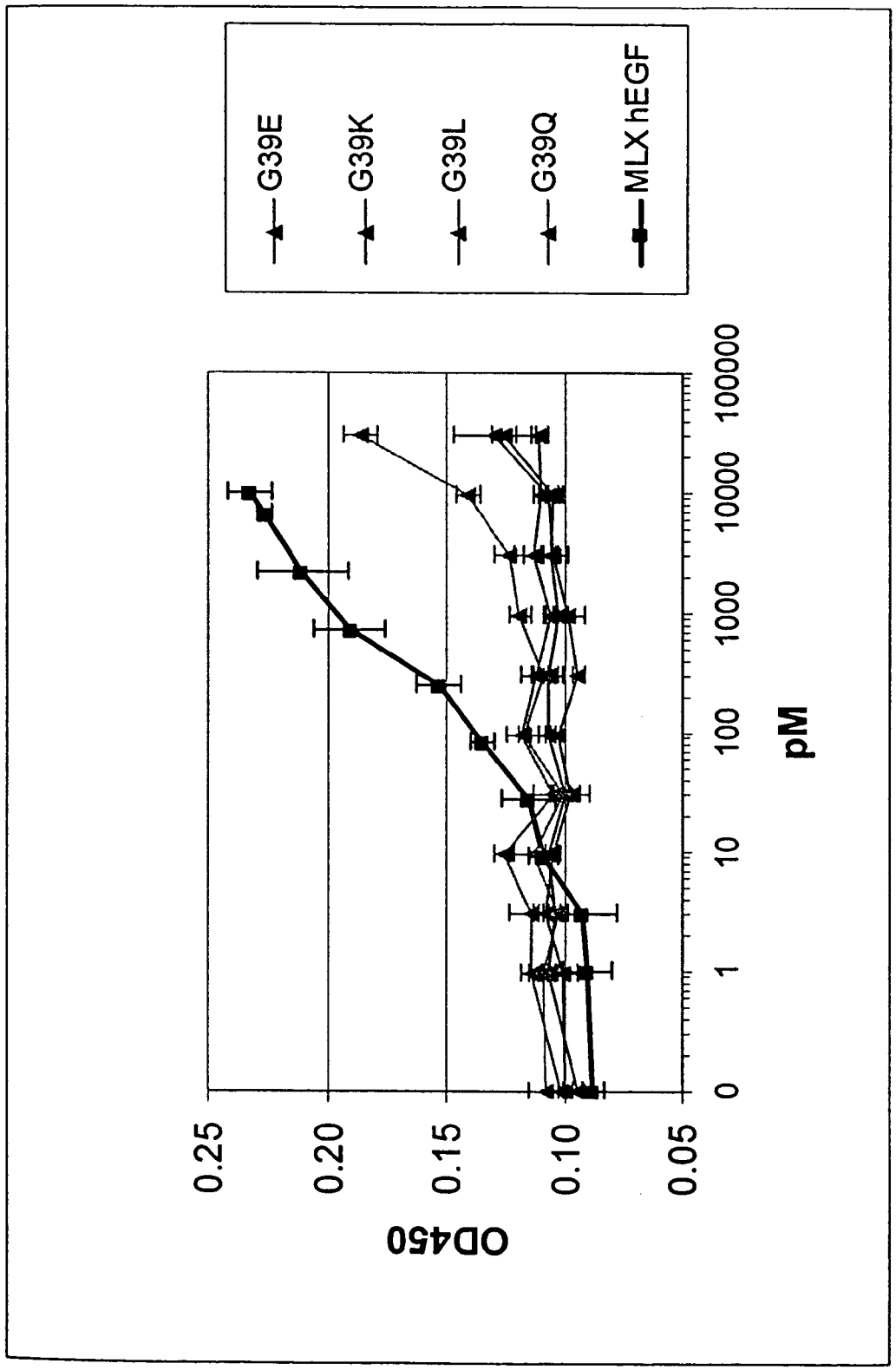
FIG. 14 is a graph showing the effect of G39 series mutants on BALB/3T3 cell proliferation (measured as the conversion of WST-1).
Figure 15:
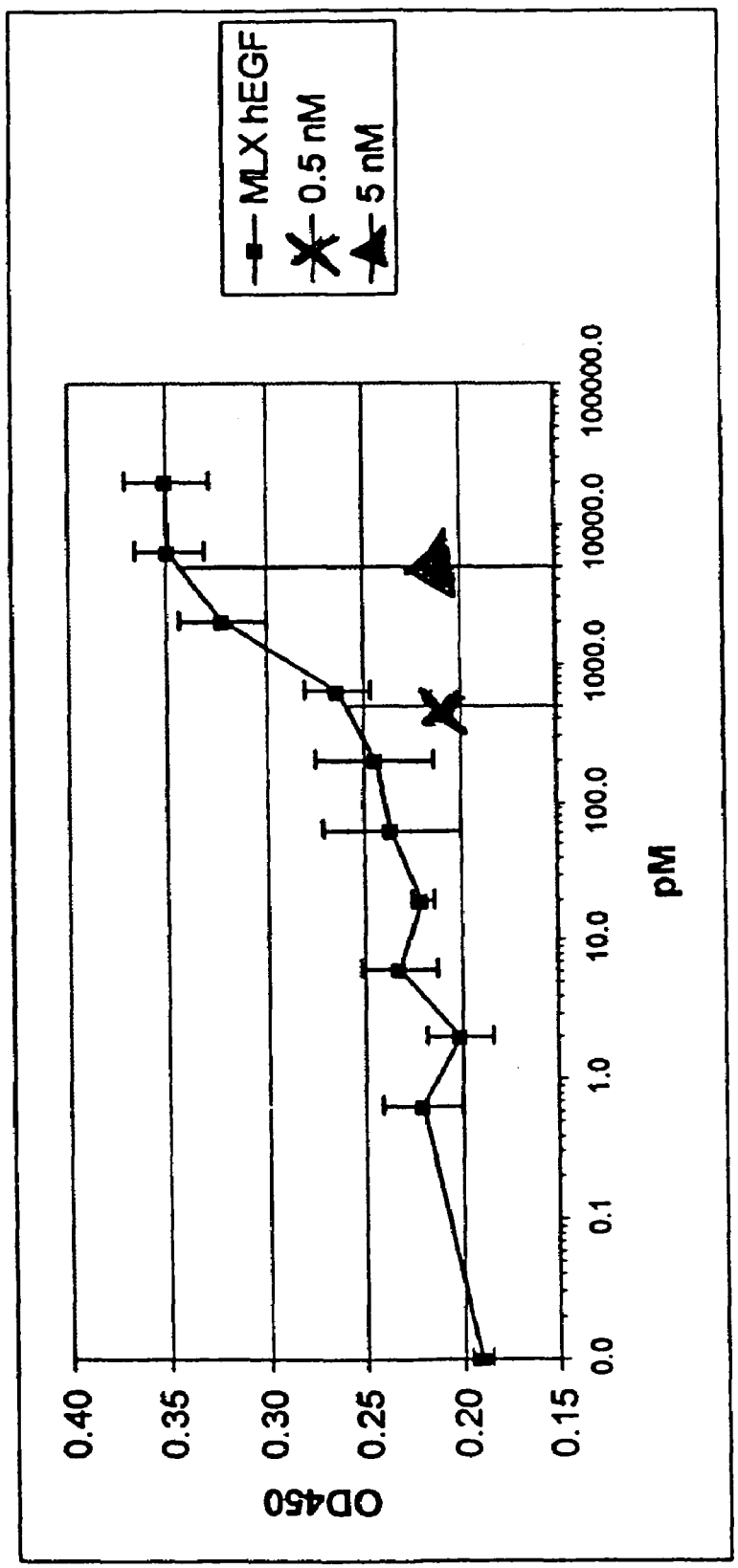
FIG. 15 is a graph showing the effect of hEGF on BALB/3T3 cell proliferation (measured as the conversion of WST-1).
Figure 16:
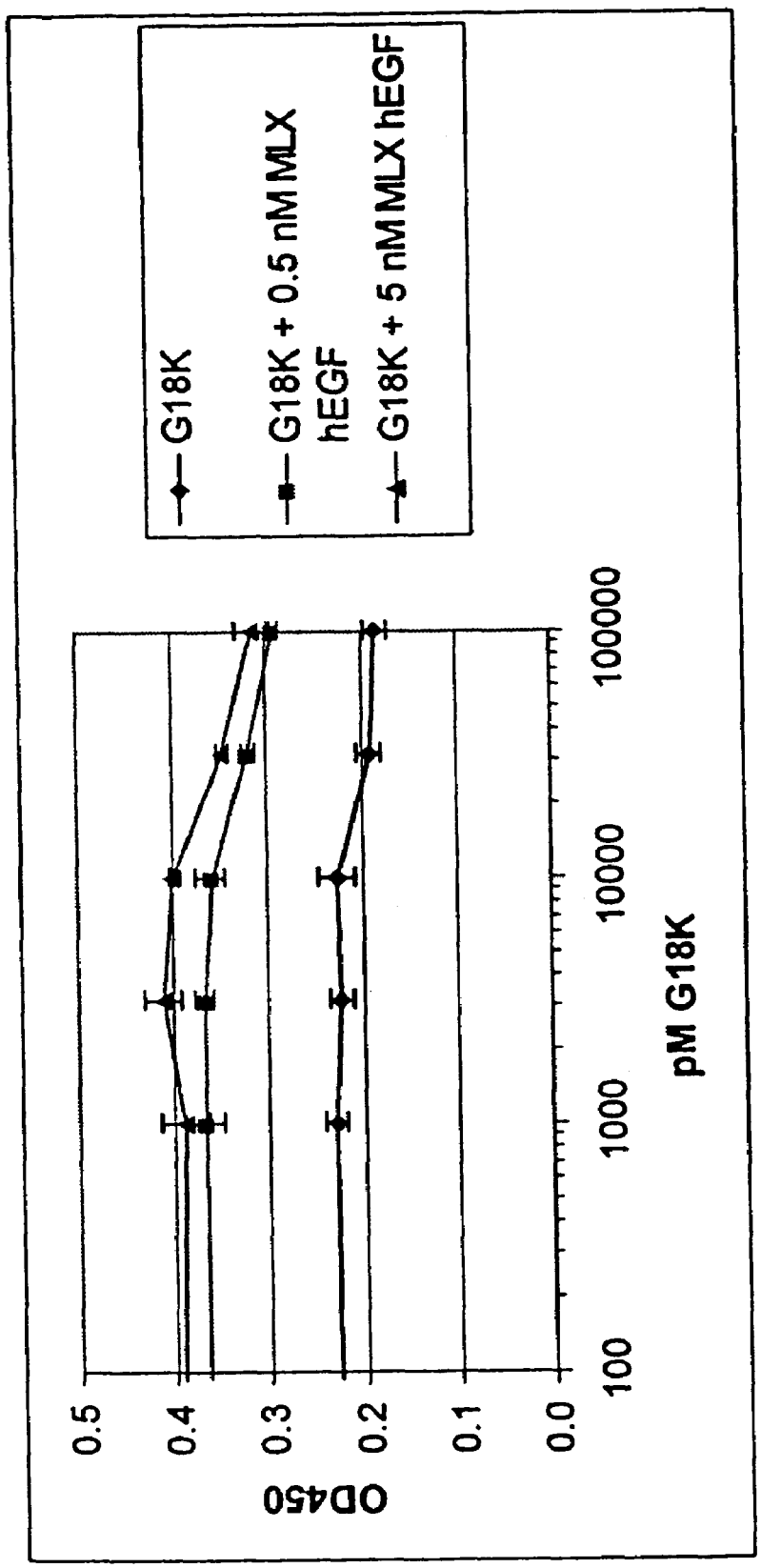
FIG. 16 is a graph showing the effect of G18K on BALB/3T3 cell proliferation (measured as the conversion of WST-1).
Figure 17:
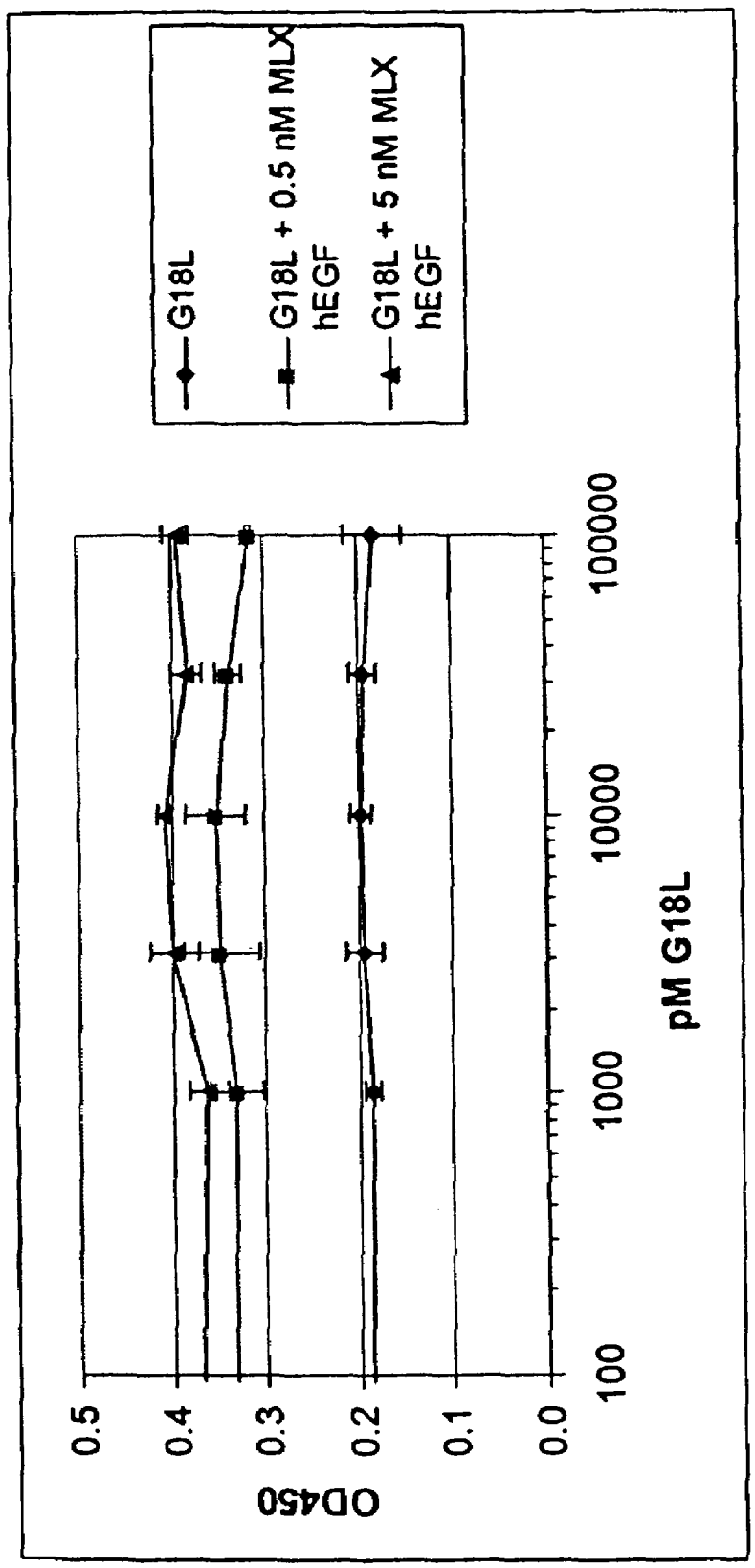
FIG. 17 is a graph showing the effect of a G18L on BALB/3T3 cell proliferation (measured as the conversion of WST-1).
Figure 18:
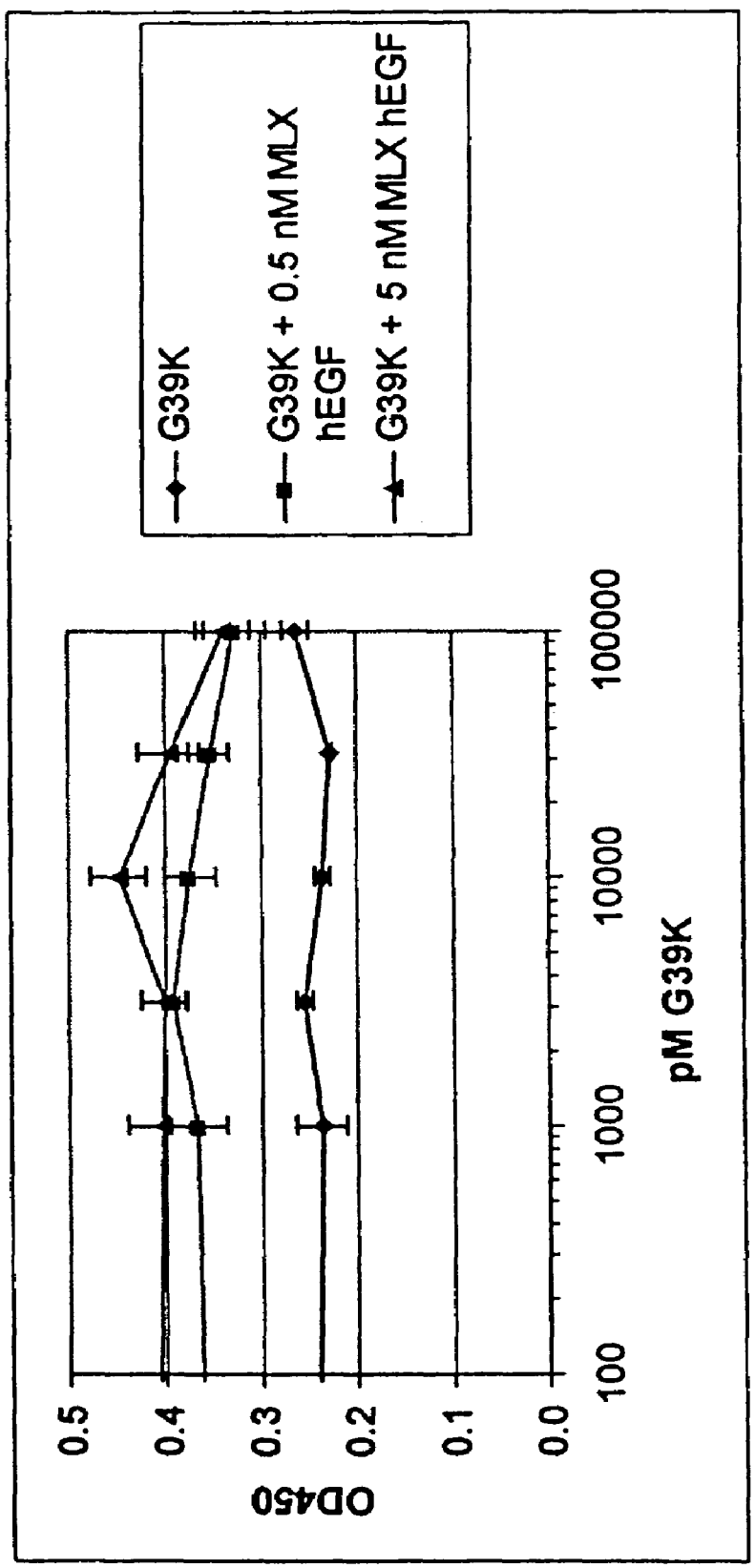
FIG. 18 is a graph showing the effect of G39K on BALB/3T3 cell proliferation (measured as the conversion of WST-1).
Figure 19:
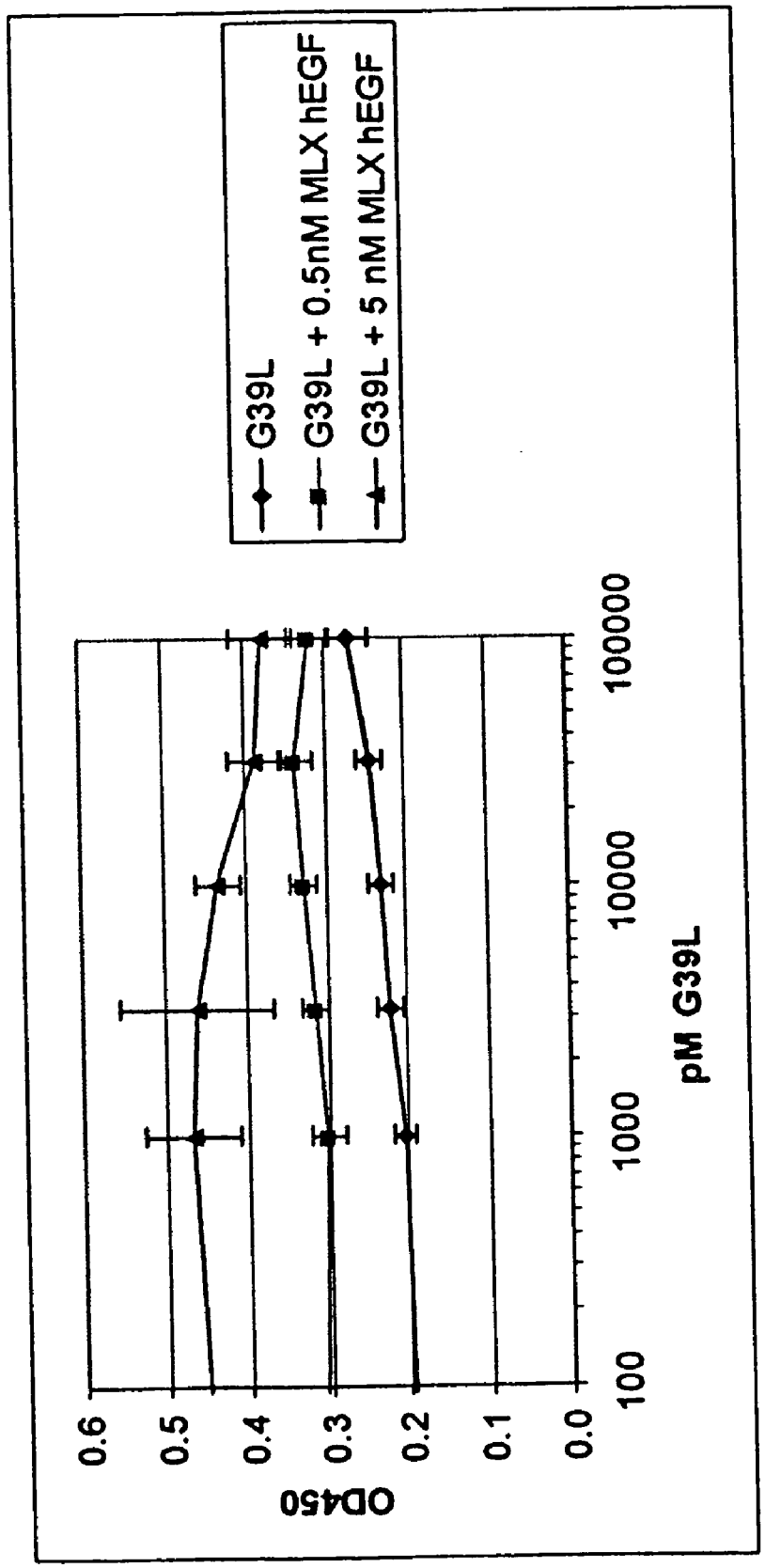
FIG. 19 is a graph showing the effect of a G39L on BALB/3T3 cell proliferation (measured as the conversion of WST-1).

A description of preferred embodiments of the invention follows.

The present invention features EGFR antagonists. These EGFR antagonists are EGFR-ligand variants. Examples of EGFR ligands include mammalian EGF (e.g. human, pig, cat, dog, mouse, horse and rat). Other examples of EGFR ligands include transforming growth factor-α (TGFα), betacellulin, heparin-binding EGF-like growth factor (HB-EGF), amphiregulin (AR) and epiregulin. Preferred ligand variants of the invention are human EGF polypeptide variants capable of selectively inhibiting EGFR-mediated biological activity.

The present invention results from the unexpected discovery that an EGFR ligand (e.g., EGF) polypeptide variant that has one or more mutations that prevent, banish or abrogate binding of the peptide to Domain III of the EGFR and, optionally, a mutation that binds, preferably tightly, to Domain I of the EGFR can result in good to excellent EGF antagonists having therapeutic properties. As such, the invention relates to EGFR antagonists having a polypeptide sequence substantially similar to EGF (or other EGFR ligand) characterized by at least one amino acid substitution, deletion or insertion that prevents the antagonist from binding Domain III of EGFR and, optionally at least one amino acid substitution, deletion or insertion that results in antagonist binding to Domain I of EGFR, preferably tight binding. An example of tight binding includes the formation of an ionic or covalent, hydrophobic, electrostatic, or hydrogen bonds between one or more amino acids of the antagonist and the receptor. Binding can be considered "tight" if the antagonist is not substantially displaced from EGFR by EGF, e.g., in an in vitro assay such as an assay described herein. The antagonist is not substantially displaced if at least 50%, preferably at least 70%, more preferably at least about 90%, such as 100%, of the antagonist remains bound to EGFR in an assay described herein. Binding can also be considered tight if the antagonist substantially displaces EGF from EGFR, e.g., in an in vitro assay such as an assay described herein. The antagonist substantially displaces EGF if at least 50%, preferably at least 70%, more preferably at least about 90%, such as 100%, of the EGF is displaced from EGFR in an assay described herein.

In one aspect, the present invention features EGF polypeptide variants having substantial amino acid sequence identity to wild-type EGF, preferably wild-type human EGF and more preferably to the 53 amino acid human wild-type EGF, and that function to inhibit EGFR-mediated biological activity. By "EGFR-mediated biological activity" as used herein is meant the intrinsic protein-tyrosine kinase activity of EGFR and its downstream signal transduction cascade which ultimately leads to DNA synthesis and cell proliferation. By "EGFR antagonist" is meant any molecule that inhibits, suppresses or causes the cessation of EGFR-mediated biological activity, e.g. by reducing, interfering with, blocking, or otherwise preventing the interaction or binding of a native or active EFGR ligand to EGFR. The use of the term "antagonist" is used herein in a functional sense and is not intended to limit the invention to compounds having a particular mechanism of action. For example, the term "antagonist" includes, but is not limited to, a molecule that functions as a competitive antagonist. A competitive antagonist binds the EGFR receptor but does not trigger the biological activity of the EGFR receptor and prevents wild-type ligands from binding and activating. The term "antagonist" may also include a molecule that causes down-regulation of the EGFR receptor such that the receptor is no longer present in the cell membrane and therefore cannot associate with its ligand to cause activation of the receptor.

EGF polypeptide variants of the invention (also referred to herein as "modified EGF polypeptides") possess a number of useful properties. For example, the polypeptide variants of the present invention can be used to treat diseases wherein overexpression of EGFR is implicated in the pathological process of the disease (e.g. cancer).

EGF polypeptide variants are provided that have substantial identity with human wild-type EGF in which the amino acid position that corresponds to amino acid Gly 18 (G18) and/or amino acid Gly 39 (G39) and/or amino acid Arg 41 (R41) and/or amino acid Val 35 (V35) of wild type human EGF is substituted with an amino acid, and wherein the polypeptide has (EGFR) antagonist activity. As used herein, the phrase "the amino acid position that corresponds to amino acid G18 and/or amino acid G39 and/or R41 and/or amino acid V35 of wild-type human EGF" means that when the unmodified EGF polypeptides from various mammalian species are aligned with human wild-type EGF for optimal comparison, the glycine, arginine or valine amino acids that appear at or near the positions that correspond to G18, G39, R41 and, optionally, V35 of human wild-type EGF may be substituted with another amino acid.

In certain preferred embodiments, G18 is replaced by glutamate (G18E), glutamine (G18Q), lysine (G18K), phenylalanine (G18F), or leucine (G18L). In a particularly preferred embodiment, G18 is replaced by phenylalanine (G18F) or leucine (G18L). In yet another preferred embodiment, G18 is replaced by phenylalanine (G18F).

Additionally or alternatively, G39 is replaced by glutamate (G39E), glutamine (G39Q), lysine (G39K), aspartic acid (G39D) or isoleucine (G39I), or leucine (G39L). In a particularly preferred embodiment G39 is replaced by phenylalanine (G39F), leucine (G39L), aspartic acid (G39D), or isoleucine (G39I). G39L is preferred.

Additionally or alternatively, R41 is replaced by aspartate (R41D).

Modifications to G18, G39 and R41 are believed to be responsible for preventing, banishing or abrogating binding of the variant to EGFR Domain III. In other words, the variant is believed to not bind to Domain III of EGFR.

Additionally or alternatively, V35 is replaced by glutamate (V35E). It is believed that the modification to V35 is responsible for tight binding of the variant to Domain I of the EGFR. In combination, then, mutations at V35 along with mutations at G18 and additionally or alternatively G39 and additionally or alternatively R41 result in a polypeptide with antagonist properties.

It is understood, however, that G18, G39 and/or V35 may be substituted with any suitable amino acid such that the EGFR antagonistic activity of the modified EGF polypeptide of the invention remain intact. While substitution of V35 with aspartic acid resulted in a loss of some of the antagonist function of the variant in at least one assay, more research is required.

Furthermore, other amino acids can be targeted. Reviewing the crystal structure of EGF and EGFR can identify additional amino acids that can be modified to remove, introduce or displace a reactive or functional group on an amino acid side chain to prevent or cause binding to the EGFR, as the case may be. It is known that changes in an adjacent or proximal amino acid can alter the confirmation of another amino acid, changing its binding properties. Thus, the variants exemplified herein are expected to be representative of a broader class of antagonists that possess the desired binding characteristics and resulting therapeutic antagonist properties. The crystal structure of EGF and EGFR is known and described, for example, in Ogiso et al., *Cell,* 110:775-787 (2002), which is incorporated herein by reference.

In addition, homologs, analogs and fragments of the preferred human EGF polypeptide variants are within the scope of the present invention. By "homologs" is meant the corresponding polypeptides of EGF from other mammalian species having substantial identity to human wild-type EGF, so long as such homologs retain EGFR antagonist activity. The EGF polypeptide sequences for various mammalian species are as follows:

```
NSDSECPLSHDGYCLHDGVCMYIEALDKYACNCVVGYIGERCQYRDLKWWELR  Human  (SEQ ID NO:1)
NSYSECPPSHDGYCLHGGVCMYIEAVDSYACNCVFGYVGERCQHRDLKWWELR  Pig    (SEQ ID NO:2)
NSYQECPPSYDGYCLYNGVCMYIEAVDRYACNCVFGYVGERCQHRDLK-WELR  Cat    (SEQ ID NO:3)
NGYRECPSSYDGYCLYNGVCMYIEAVDRYACNCVFGYVGERCQHRDLK-WELR  Dog    (SEQ ID NO:4)
NSYPGCPSSYDGYCLNGGVCMHIESLDSYTCNCVIGYSGDRCQTRDLRWWELR  Mouse  (SEQ ID NO:5)
NSYQECSQSYDGYCLHGGKCVYLVQVDTHACNCVVGYVGERCQHQDLR-----  Horse  (SEQ ID NO:6)
NSNTGCPPSYDGYCLNGGVCMYVESVDRYVCNCVIGYIGERCQHRDLRWWKLR  Rat    (SEQ ID NO:7);
```

"Analogs" is meant to include polypeptide variants which differ by one or more amino acid alterations, e.g., substitutions, additions or deletions of amino acid residues that still maintain the EGFR antagonistic properties of the relevant peptides.

Besides the mutations at positions G18, G39, R41 and V35 of EGF polypeptide variants, additional mutations are possible which will leave the EGFR inhibitory activity or antagonist activity of the EGF polypeptide variant substantially intact. These mutations may take the form of single or multiple substitutions, deletions, or insertions. Amino acid substitutions may take the form of conservative or non-conservative amino acid substitutions at one or more locations on the polypeptide. As used herein the term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine, and leucine for another non-polar residue. Likewise, examples of conservative substitutions include the substitution of one polar (hydrophilic) residue for another such as between arginine and lysine, between glutamine and asparagine, and between glycine and serine. Additionally, the substitution of a basic residue such as lysine, arginine or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, methionine for a polar (hydrophilic) residue such as cysteine, glutamine, glutamic acid or lysine and/or a polar residue for a non-polar residue.

Additionally, it is believed that the N-terminus of EGF does not participate in binding to the EGFR and is thought to move freely, even upon ligand binding. Thus, deletion of the N-terminus of the ligand is envisioned as an example of a further modification that will not detract from the antagonist properties of the variant. Modification of the N-terminus to add one or more binding functionalities that will cause or assist the N-terminus to bind to EGFR can also be made. The C-terminus is believed to be implicated in Domain III binding. Thus, modifications to the C-terminus can also be envisioned to be changed to prevent, banish or abrogate Domain III binding.

The therapeutic qualities of G18, V35, G39 or R41 EGF peptide variants may also be further improved through amino acid substitutions, deletions and insertions at locations in addition to G18, V35, G39 or R41. These improved therapeutic qualities include, but are not limited to, enhanced affinity, increased half-life, increased solubility, and increased bioavailability.

EGF polypeptide variants in accordance with the present invention can be designed and tested using any number of methods. Amino acid substitutions, deletions or insertions at positions G18, V35, G39 and/or R41 or at any other suitable positions that contribute to the EGFR antagonistic or EGFR inhibitory activity of an EGF polypeptide variant of the invention can be identified by methods known in the art such as site directed mutagenesis. The resulting mutated EGF polypeptides are then tested for EGFR antagonistic activity using in vitro screening assays such as those described herein or any other suitable screening assay.

The data described herein indicates that EGF polypeptides having a combination of amino acid substitutions at V35 as well as at G18, G39 and/or R41 can inhibit the activation of the kinase moiety of EGFR in the presence of wild-type recombinant human EGF (MLX hEGF). Polypeptides of the invention were also tested in cell proliferation assays and shown to inhibit the proliferation of cells. Competition kinase activity and cell proliferation assays show that polypeptides of the invention compete with MLX hEGF to inhibit the activation of the kinase moiety of EGFR as well as cell proliferation. The inhibitory or other antagonistic activity of a candidate polypeptide of the invention can be assessed in any assay or method described herein, or in any other suitable assay or other method with EGFR, and compared to the activity in the presence of wild-type human EGF polypeptide.

As described above, the modified EGF polypeptide variants of the present invention, their homologs and analogs have substantial identity to wild-type EGF, preferably wild-type human EGF. As used herein, "substantial identity" means at least 60% sequence identity, preferably at least 70% identity, preferably at least 80% and more preferably at least 90% sequence identity to the amino acid sequence of wild-type human EGF, while maintaining EGFR inhibitory or other EGFR antagonist activity. In other embodiments, the polypeptide variants of the present invention have at least 91%, at least 92%, at least 93%, at least 94%, at least 95% at least 96%, at least 97%, or at least 98% amino acid identity to the amino acid sequence of wild-type human EGF, while maintaining EGFR inhibitory or other EGFR antagonist activity. The percent identity of two nucleotide or amino acid sequences can be determined by aligning the sequences for optimal comparison purposes (e.g., gaps can be introduced in the sequence of a first sequence). The amino acids at corresponding positions are then compared, and the percent identity between the two sequences is a function of the number of identical positions shared by the sequences (i.e., % identity=# of identical positions/total # of positions×100). The actual comparison of the two sequences can be accomplished by well-known methods, for example, using a mathematical algorithm. A preferred, non-limiting example of such a mathematical algorithm is described in Karlin et al., *Proc. Natl. Acad. Sci. USA,* 90:5873-5877 (1993). Such an algorithm is incorporated into the BLASTN and BLASTX programs (version 2.2) as described in Schaffer et al., *Nucleic Acids Res.* 29:2994-3005 (2001).

The EGF polypeptide variants of the invention may be produced by several techniques. In one preferred embodiment, the EGF polypeptide variants of the invention are produced by expression in a suitable host of a gene coding for the relevant polypeptide variant. Such a gene is most readily prepared by site-directed mutagenesis of wild-type human EGF gene as described herein. However, the EGF polypeptide variants of the invention may be produced in whole or in part by chemical synthetic techniques such as by a Merrifield-type synthesis. Chemical synthesis of all or a portion of a modified EGF polypeptide of the invention may be particularly desirable in the case of the use of a non-naturally occurring amino acid substituent in the polypeptide variant.

The modified EGF polypeptides of the present invention can be designed and tested using any number of methods. Amino acid substitutions at positions G18, V35, G39 or at any other suitable positions that contribute to the EGFR antagonistic or other EGFR inhibitory activity of a modified EGF polypeptide can be generated by methods known in the art, such as site directed mutagenesis. The resulting mutated EGF polypeptides are then tested for EGFR antagonistic activity using an in vitro screening assay such as those described herein or any other suitable screening assay.

The present invention also provides nucleic acid molecules encoding a polypeptide having substantial identity with an EGFR ligand variant, such as a modified EGF polypeptide of the invention and having EGFR antagonistic activity. The nucleic acid molecules of the present invention can be RNA, for example, mRNA, or DNA. DNA molecules can be double-stranded or single-stranded. The nucleic acid molecule can also be fused to a marker sequence, for example, a sequence that encodes a polypeptide to assist in isolation or purification of the polypeptide. Such sequences include, but are not limited to, those that encode a glutathione-S-transferase (GST) fusion protein, those that encode a hemagglutinin A (HA) polypeptide marker from influenza, and sequences encoding a His tag.

It will be appreciated by those skilled in the art that the design of the expression vector can depend on such factors as the choice of the host cell to be transformed and the level of expression of polypeptide desired. The expression vectors of the invention can be introduced into host cells to thereby produce the modified EGFR ligand or EGF polypeptides of the invention, including fusion polypeptides, encoded by nucleic acid molecules as described herein. Molecular biology techniques for carrying out recombinant production of the modified EGF polypeptides of the invention are well known in the art and are described for example, in, Sambrook, et al., *Molecular Cloning: A Laboratory Manual* (Cold Spring Harbor Lab Press); $3^{rd}$ ed., 2000).

The present invention also pertains to pharmaceutical compositions comprising the EGF polypeptide variants described herein. For instance, an EGF polypeptide variant of the invention can be formulated with a physiologically acceptable carrier or excipient to prepare a pharmaceutical composition. The carrier and composition can be sterile. The formulation should suit the mode of administration.

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylase or starch, dextrose, magnesium stearate, talc, silicic acid, viscous paraffin, perfume oil, fatty acid esters, hydroxymethylcellulose, polyvinyl pyrrolidone, etc., as well as combinations thereof. In addition, carriers such as liposomes and microemulsions may be used. The polypeptide variants of the invention may also be covalently attached to a protein carrier such as albumin, or a polymer, such as polyethylene glycol so as to minimize premature clearing of the polypeptides. The pharmaceutical preparations can, if desired, be mixed with auxiliary agents, e.g. lubricants, preservatives, stabilizers, wetting agents, emulsifiers, salts for influencing osmotic pressure, buffers, coloring, flavoring and/or aromatic substances and the like that do not deleteriously react with the active agent in the composition (i.e., a polypeptide and/or nucleic acid molecule of the invention).

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, polyvinyl pyrrolidone, sodium saccharine, cellulose, magnesium carbonate, etc.

Methods of introduction of these compositions include, but are not limited to, transdermal, intramuscular, intraperitoneal, intraocular, intravenous, subcutaneous, topical, oral and intranasal. Other suitable methods of introduction can also include gene therapy (as described below), rechargeable or biodegradable devices, particle acceleration devices ("gene guns") and slow release polymeric devices. The pharmaceutical compositions of this invention can also be administered as part of a combination therapy with other compounds.

The EGF polypeptide variants of the present invention can be formulated in accordance with the routine procedures as a pharmaceutical composition adapted for administration to human beings. For example, compositions for intravenous administration typically are solutions in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentration in a hermetically sealed container such as an ampoule or sachette indicating the quantity of active compound (polypeptide and/or nucleic acid). Where the composition is to be administered by infusion, it can be dispensed with an infusion bottle containing sterile pharmaceutical grade water, saline or dextrose/water. Where the composition is administered by injection, an ampoule of sterile water for injection or saline can be provided so that the ingredients may be mixed prior to administration.

The EGF polypeptide variants described herein can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The EGF polypeptide variants of the invention are administered in a therapeutically effective amount. The amount of polypeptide that will be therapeutically effective in the treatment of a particular disorder or conditions will depend on the nature of the disorder or condition, and can be determined by standard clinical techniques. In addition, in vitro or in vivo assays may optionally be employed to help identify optimal dosage ranges. The precise dose to be employed in the formulation will also depend on the route of administration, and the seriousness of the symptoms of the disease or condition, and should be decided according to the judgment of a practitioner and each patient's circumstances. Effective doses may be extrapolated from dose-response curves derived from in vitro or animal model test systems.

The present invention also pertains to methods of treatment (prophylactic, diagnostic, and/or therapeutic) for conditions characterized by EGFR overexpression. A "condition characterized by EGFR overexpression" is a condition in which the presence of an EGF polypeptide variant of the invention is therapeutic. Such conditions include many types of cancer. For example, many tumors of mesodermal and ectodermal origin overexpress the EGF receptor. The EGF receptor has been shown to be overexpressed in many gliomas, squamous cell carcinomas, breast carcinomas, melanomas, invasive bladder carcinomas and esophageal cancers. In addition, studies with primary human mammary tumors have shown a correlation between high EGF receptor expression and the presence of metastases, higher rates of proliferation, and shorter patient survival. Overexpression of EGF receptors has also been implicated in a variety of other disorders such as psoriasis, and fibrosis.

The term "treatment" as used herein, refers not only to ameliorating symptoms associated with the disease or condition, but also preventing or delaying the onset of the disease, and also lessening the severity or frequency of symptoms of the disease or condition. More than one modified EGF polypeptide of the present invention can be used concurrently as co-therapeutic treatment regimen, if desired. As used herein, a "co-therapeutic treatment regimen" means a treatment regimen wherein two drugs are administered simultaneously, in either separate or combined formulations, or sequentially at different times separated by minutes, hours or days, but in some way act together to provide the desired therapeutic response. The polypeptides of the invention may also be used in conjunction with other drugs that inhibit various aberrant activities of the EGFR receptor. Such additional drugs include but are not limited to EGFR—specific antibodies, small molecule kinase inhibitors, and traditional chemotherapeutic agents.

The therapeutic compound(s) of the present invention are administered in a therapeutically effective amount (i.e., an amount that is sufficient to treat the disease or condition, such as by ameliorating symptoms associated with the disease or condition, preventing or delaying the onset of the disease or condition, and/or also lessening the severity or frequency of symptoms of the disease or condition). The amount that will be therapeutically effective in the treatment of a particular individual's disease or condition will depend on the symptoms and severity of the disease, and can be determined by standard clinical techniques. In addition, in vitro or in vivo assays may optionally be employed to help identify optimal dosage ranges. The precise dose to be employed in the formulation will also depend on the route of administration, and the seriousness of the disease or condition, and should be decided according to the judgment of a practitioner and each patient's circumstances. Effective doses may be extrapolated from dose-response curves derived from in vitro or animal model test systems.

The therapeutic compounds of the present invention can be used either alone or in a pharmaceutical composition as described above. For example, the gene for a modified EGF polypeptide of the present invention, either by itself or included within a vector, can be introduced into cells (either in vitro or in vivo) such that the cells produce the desired polypeptide. If desired, cells that have been transfected with the nucleic acid molecule of the present invention can be introduced (or re-introduced) into an individual affected with the disease.

Other gene transfer systems, including viral and nonviral transfer systems, can be used. Alternatively, nonviral gene transfer methods, such as calcium phosphate co-precipitation, mechanical techniques (e.g., microinjection); electroporation; membrane fusion-mediated transfer via liposomes; or direct DNA uptake, can also be used to introduce the desired nucleic acid molecule into a cell.

In another aspect, the invention relates to polypeptide variants of EGFR ligands that possess EGFR antagonistic properties other than the EGF polypeptide variants previously described herein. Polypeptide variants of EGFR ligands such as transforming growth factor-α (TGFα), betacellulin, heparin-binding EGF-like growth factor (HB-EGF), amphiregulin (AR) and epiregulin may be designed, and assayed for antagonistic properties in accordance with the methods previously described herein and in the accompanying examples, and used as an EGFR antagonist. The EGFR ligands have amino acid sequences that include glycines at positions that corresponds to G18 and/or G39 of human wild-type EGF as well as an arginine that correspond to R41. The residues that correspond to V35 in human wild-type EGF vary in the different EGFR ligands, including a glutamate in betacellulin. As used herein "a position that corresponds to G18 and/or G39 of human wild-type EGF" means that when the EGFR ligand peptides from (TGFα), betacellulin, HB-EGF, AR and epiregulin, are aligned with human EGF for optimal comparison, the amino acids that correspond to G18, V35, G39 and R41 of human EGF may be substituted with another amino acid as previously described herein. The unmodified polypeptide sequences of the above-mentioned EGFR ligands as compared to human EGF are as follows (SEQ ID NOS:1, 8, 9, 10, 11, and 12, respectively):

ligands and as if repeated herein for each EGFR ligand variant. Such EGFR ligand polypeptide variants, their homologs and analogs are useful as pharmaceutical compositions and in methods of treating diseases associated with EGFR overexpression, as discussed above with respect to EGF ligands and as if repeated herein in its entirety for each EGFR ligand.

EXAMPLES

Example 1

EGF Variant Cloning

The human epidermal growth factor (hEGF) gene was chemically synthesized and ligated into the Pet-9a vector (Novagen, EMD Biosciences, San Diego, Calif.) at the NdeI and BamHI cloning sites. The hEGF gene contained the

```
EGF           ----------------------------------------------------------
TGFa          ----------------------------------------------------------
Epiregulin    ------------------------------------------------------MTAG     4
Betacellulin  ------------------------------------------------------MDRA     4
Amphiregulin  MRAPLLPPAPVVLSLLILGSGHYAAGLDLNDTYSGKREPFSGDHSADGFEVTSRSEMSSG   60
HB-EGF        --MKLLPSVVLKLFLAAVLSALVTG--------------------ESLERLRRGLAAGT    37

EGF           ----------------------------------------------------------
TGFa          ---------------------------------------------VVS---------     3
Epiregulin    RRMEMLCAGRVPALLLCLG-----FHLLQA---------------VLS--TTVIPSCIPG   42
Betacellulin  ARCSGASS-LPLLLALALG-----LVILHC---------------VVADGNSTRSPETNG  43
Amphiregulin  SEISPVSEMPSSSEPSSGADYDYSEEYDNEPQIPGYIVDDSVRVEQVVKPPQNKTESENT  120
HB-EGF        SNPDPPTVSTDQLLPLGGGRDRKVRDLQEA---------------DLDLLRVTLSSKPQA   82

EGF           ------------------NSDSECPLSHDGYCLHDGVCMYIEALDKYACNCVVGYIGE    40
TGFa          ------------------HFNDCPDSHTQFCFH-GTCRFLVQEDKPACVCHSGYVGA    41
Epiregulin    ESSDNCTALVQTEDNPRVAQVSITKSSSDMNGYCLH-GQCIYLVDMSQNYCRCEVGYTGV  101
Betacellulin  LLCGDPEENCAATTTQSKRKGHFSRCPKQYKHYCIK-GRCRFVVAEQTPSCVCDEGYIGA  102
Amphiregulin  SDKPKRKKKGGKNGKNRRNRKKKNPCNAEFQNFCIH-GECKYIEHLEAVTCKCQQEYFGE  179
HB-EGF        LATPNKEEHGKRKKKGKGLGKKRDPCLRKYKDFCIH-GECKYVKELRAPSCICHPGYHGE  141

EGF           RCQYRDLKWWELR---------------------------------------------    53
TGFa          RCEHADLLA-------------------------------------------------    50
Epiregulin    RCEHFFLTVHQPLSKEYVALTVILIILFLITVVG-STYYFCRWYRNRKSKEPKKEYERVT  160
Betacellulin  RCERVDLFYLRGDRGQILVICLIAVMVVFIILVI-GVCTCCHPLRKRRKRKKKEEEMETL  161
Amphiregulin  RCGEKSMKTHSMIDSSLSKIALAAIAAFMSAVILTAVAVITVQLRRQYVRKYEGEAEERK  239
HB-EGF        RCHGLSLPVENRLYTYDHTTILAVVAVVLSSVCL-LVIVGLLMFRYHRRGGYDVENEEKV  200

EGF           -----------------   (SEQ ID NO: 1)
TGFa          -----------------   (SEQ ID NO: 8)
Epiregulin    SGDPELPQV--------  169  (SEQ ID NO: 9)
Betacellulin  GKDITPINEDIEETNIA  178  (SEQ ID NO: 10)
Amphiregulin  KLRQENGNVHAIA----  252  (SEQ ID NO: 11)
HB-EGF        KLGMTNSH---------  208  (SEQ ID NO: 12)
```

The residues that correspond to G18, V35, G39, and R41 in hEGF are given in the following table.

TABLE 1

| EGFR Ligand | Position corresponding to G18 in hEGF | Residue corresponding to V35 in hEGF | Position corresponding to G39 in hEGF | Position corresponding to R41 in hEGF |
| --- | --- | --- | --- | --- |
| TGFα | 19 | S36 | 40 | 42 |
| Epiregulin | 79 | V96 | 100 | 102 |
| Betacellulin | 80 | E97 | 101 | 103 |
| Amphiregulin | 157 | Q174 | 178 | 180 |
| HB-EGF | 119 | P136 | 140 | 142 |

Polypeptide variants of EGFR ligands can be designed and tested for EGFR antagonistic activity as described above for EGF ligands. Additional modifications can be made to these EGFR ligand variants as described above with respect to EGF OmpA leader sequence followed by an N-terminal 6x-his tag and a factor Xa cleavage site. Thus all hEGF and variants produced in this manner are fused at the N-terminus to the following peptide: HHHHHHIEGR (SEQ ID NO: 13). We have observed that hEGF fusion (MLX hEGF) performs in an identical manner in all of our assays compared to commercially available hEGF (Data not shown). This original clone, designated pMLPP1, was used as a basis for creating EGF variants using the QuickChange mutagenesis kit (Stratagene, La Jolla, Calif.). For protein production the EGF plasmids were transformed into E. coli strain BL21 (DE3) pLysS (Novagen). The plasmid containing the EGF variant genes contains the gene for kanamycin resistance as the selectable marker. In addition, the E. coli strain used is chloramphenicol resistant. Competent E. coli cells were transformed with the plasmid by heat shock (42° C. for 45 seconds). Transformed cells were selected by exposure to both kanamycin and chloramphenicol.

Expression Screening 3 or more colonies were picked from each transformation plate and grown at 37° C. overnight in test tube cultures containing LB+Km25+Cm30. These cultures were used to inoculate shake flask cultures in the same medium and, 0.2 uM IPTG was added to the culture when OD 600>0.25(2-4 hrs). The cultures were grown overnight, centrifuged, and the supernatants were tested for EGF production via dot blot using the Mouse Western Breeze Chromogenic Immunodetection System (Invitrogen, Carlsbad, Calif., cat#WB7103) with Primary antibody: 1:1000 mouse anti-penta his antibody (Qiagen, Valencia, Calif., cat#34660).

Production of EGF

The highest EGF expression clones were streaked to a fresh plate, and single colonies were inoculated into test tube cultures containing 15 ml LB+Km25+Cm30. After growth overnight, samples of culture were frozen for stocks, and for plasmid preps to confirm the identities of the EGF variant gene inserts. The remaining cultures were used to inoculate production cultures in TB+Km25+Cm30. Again, 0.2 uM IPTG was added when OD600>0.25 (about 2-4 hrs), and the cultures were grown overnight. Culture supernatants were collected after centrifugation and production was confirmed by dot blot with mouse anti-penta his antibody.

EGF Protein Purification 3 ml of Ni-NTA resin (Qiagen #30230) was used to pack 5 ml columns (Qiagen cat#34964) which were equilibrated with PBS pH 8.0. Culture supernatants were adjusted to pH 7.5-8.0 with 1N HCL before loading on columns. Columns were washed with PBS and PBS+10 mM imidazole; EGF variant proteins were eluted from columns with PBS+250 mM imidazole. Bradford protein assays were used to monitor protein concentrations.

Protein Concentration and Buffer Exchange

Column eluents were dialyzed in PBS at 4° C. with one buffer exchange, and then concentrated with 3000MWCO Macrosep centrifuge devices (ISC# OD003c41). The final product was tested for protein concentration by BCA protein assay and for purity by SDS-PAGE.

Example 2

EGFR Kinase ELISA

To examine the kinase activity of epidermal growth factor receptor (EGFR) in the presence of hEGF and EGF variants, an ELISA was developed. Briefly, an ELISA plate is coated with poly-glu, tyr (4:1) which serves as a substrate for tyrosine phosphorylation by the EGFR. The ELISA plate is then incubated with assay buffer, which includes an ATP generating system, EGFR in the form of A431 cell membrane receptor preparations, and EGF variant. After a 15 minute incubation ATP is added to the reaction to allow the kinase activity to proceed. Anti-phosphotyrosine antibody is added to bind to the phosphorylated tyrosine bound to the plate. Anti-mouse HRP conjugate antibody is added as the detection antibody, which is visualized with the addition of tetramethyl benzidine (TMB).

The glycine at position 18 was replaced by glutamate (G18E), glutamine (G18Q), lysine (G18K), phenylalanine (G18F), and leucine (G18L). These variants were tested in the kinase assay described above and compared with recombinant wild-type human EGF (MLX hEGF). It can be seen in the figures that the G18Q variant had slight activity at the highest concentrations tested. Other variants were unable to activate the EGFR kinase.

The following variations in the glycine at position 39 were made: G39E, G39Q, G39K, and G39L. These were also tested in the kinase assay, and the results were shown in the figures. In these assays, G39K and G39E had some slight activity; the others were unable to activate the EGFR kinase, including V35EG39L.

Example 3

EGFR Kinase Competition ELISA

The EGFR kinase competition assay is basically the same as outlined above in the description of the kinase ELISA. The difference is that in the initial incubation with the EGFR and EGF variant, 50 nM human EGF is added which competes with the EGF variant for binding to the EGFR. Both the variant EGF and the human EGF are added to the assay plate before the addition of the EGFR and assay buffer, making sure neither ligand has an advantage in binding to the EGFR.

All five variants at G18 and four variants at G39 were tested in kinase competition assays. The results from G18E, G18F, G18L, and G39L are shown in the figures. In the data summarized here and in similar experiments, G18F and G18L show a slight indication of competition at the highest concentrations used, and G39L and V35EG39L demonstrate a marked interference with hEGF-related stimulation of EGFR kinase.

Example 4

EGF-stimulated Cell Proliferation Assays

The HER5 cell line, a murine fibroblast line (derived from the NR-6 line) that has been stably transfected to express the human EGF receptor was provided by Dr. M. C. Hung (MD Anderson Cancer Center). Stock cultures of HER5 were propagated in D-MEM/F12 medium containing 10% fetal bovine serum, 100 units/ml of penicillin and 100 ug/ml of streptomycin in a water-jacketed incubator at 37° C. in a humidified 5% $CO_2$ atmosphere. For HER5 proliferation assays, the cells were changed into DMEM/F12 without serum for 24 hours. Cells were then trypsinized and suspended at 1E5 cells/ml. Serial dilutions of hEGF (PeproTech, Rocky Hill, N.J.), His-tagged hEGF, test proteins were prepared in serum-free DMEM/F12 at 2-fold the final concentration and plated into the wells of 96-well plates. Fifty microliters of cell suspension (5000 cells) were added to appropriate wells bringing the total volume to 100 ul at the desired concentrations. Plates were incubated for a 48 hour proliferation period. Cell proliferation was determined by addition of 10 ul/well of WST-1 Cell Proliferation Reagent (Roche Applied Sciences, Indianapolis, Ind.) for the last three hours of the proliferation period. WST-1 is a tetrazolium salt that is cleaved to formazan dye by mitochondrial dehydrogenases in viable cells. The amount of formazan was measured at 450 nm using a microplate reader (Dynex Technologies) with MRX Revelation software.

The murine fibroblast line BALB/3T3 clone A31 (ATCC CCL-163) is cultured in D-MEM (4 mM L-glutamine, 4.5 g/L glucose, 1.5 g/L sodium bicarbonate) supplemented with 10% fetal calf serum at 37° C., 5% CO2 in air. For BALB/3T3 proliferation assays, 3000 cells were plated per well in 96-well plates with 100 ul of complete media and incubated for 20-24 hours. Media was aspirated from the wells, and the cells were washed once with DPBS. Serial dilutions of human EGF, His-tagged hEGF, or test proteins were added in 100 ul. Assay plates were incubated for 48 hours and cell proliferation was determined with WST-1 cell proliferation reagent (10 ul/well, 5 hr incubation). The absorbance at 450 nm was read with a microplate reader.

It can be seen from the figures that G18K, G18L, and G18F have the least potency of the 5 G18 variants tested in the HER5 proliferation assay. Similarly, G39K and G39L have the least potency in that series. All the G18 and G39 variants except for G18Q and G39Q were inactive in the BALB/3T3 assays.

Example 5

Proliferation Competition Assays

The BALB/3T3 proliferation assay was modified to test variants for competition with hEGF in the stimulation of BALB/3T3 cell proliferation. Serial dilutions of the test mutants were tested for proliferation in the presence of 0 nM, 0.5 nM, and 5 nM of the MLX-hEGF. BALB/3T3 cells were suspended at 3E4 cells/ml in complete serum media. 100 ul of cell suspension was plated per well in 96-well plates and incubated for 20-24 hours. Media was then aspirated from the wells, and the cells were washed once with DPBS. His-tagged wild-type hEGF at twice the final concentration was added in 50 ul/well. Serial dilutions of test mutants were prepared at twice the final concentration in serum-free media and 50 ul was added per well, bringing the final volume per well to 100 ml at the target concentrations of wt-hEGF and test mutants. Assay plates were incubated for 48 hours and cell proliferation was determined with WST-1 cell proliferation reagent (10 ul/well, 5 hr incubation). The absorbance at 450 nm was read with a microplate reader.

For the competition assays in BALB/3T3 cells, two concentrations of hEGF were chosen, 0.5 and 5.0 nM based on the dose response curve shown in the figures. Apparent competition was observed at both hEGF concentrations with G18K and G39K, but was only seen in at 0.5 nM hEGF with G18L and G39L.

Example 6

Inhibition of Cell Proliferation of A431 Cells with G18F Polypeptide Variant

A-431 cells are an epidermoid carcinoma cell line obtained from the American Type Culture Collection. The method for A431 cell proliferation inhibition is as follows. Cells are transferred to serum-free media (SFM) approx 20 hrs prior to use. Serial dilutions of test proteins (and pos. and neg. controls) are prepared to deliver twice the final concentration in 50 ul in SFM. The treatment solutions are added to appropriate wells of 96-well microtiter plates. The cells are then released from their culture plates with Trypsin-EDTA solution, centrifuged, resuspended at 1E5 c/ml in SFM and 50 ul (5000 cells) are added to each well. This brings the concentration in the wells to 1×. The plates are then incubated for 48 hours in the incubator (37C/5% CO2). 10 ul of WST-1 reagent (Roche) is added to each well for the final three hours of the proliferation period. The OD is then read at 450 nm.

Figure 20:
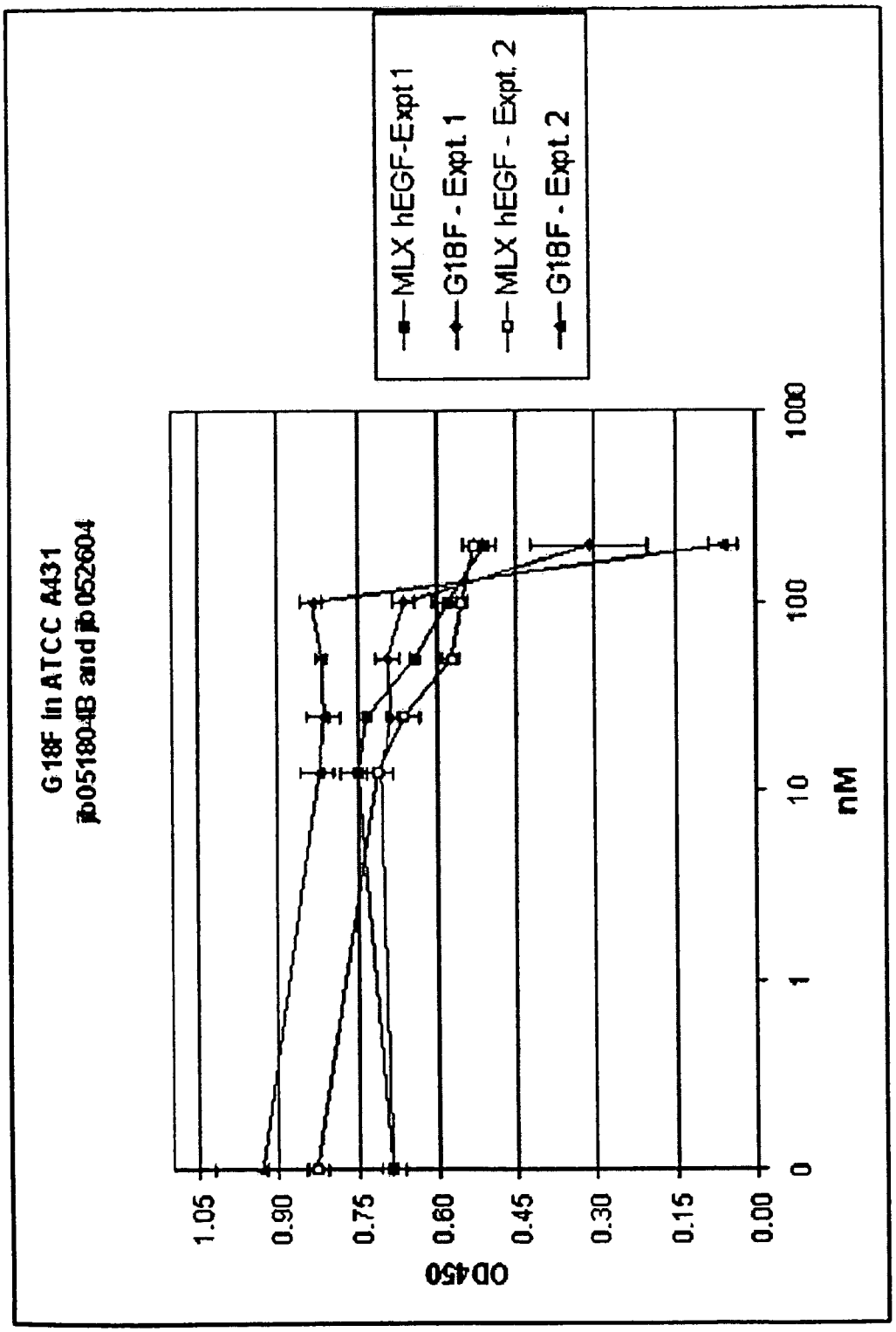
FIG. 20 is a graph showing the effect of G18F on A431 cell proliferation (measured as the conversion of WST-1).

The results shown in FIG. 20 indicate that the G18F human EGF polypeptide variant has a dramatic effect on the inhibition of A431 cell proliferation.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. An EGFR ligand polypeptide variant having an amino acid sequence with substantial identity to wild-type EGF characterized by an amino acid substitution, deletion or insertion at the amino acid position that corresponds to amino acid Gly 18, amino acid Gly 39 or amino acid Arg 41 of wild-type EGF that prevents the variant from binding Domain III of EGFR and an amino acid substitution, deletion or insertion at the amino acid position that corresponds to amino acid Val 35 of wild-type EGF that results in the variant binding to Domain I of EGFR, wherein the variant is an EGFR antagonist.

2. A human epidermal growth factor polypeptide variant having an amino acid sequence with substantial identity to wild-type EGF in which the amino acid position that corresponds to amino acid Gly 18, amino acid Val 35, or amino acid Gly 39 of human wild-type epidermal growth factor is substituted with another amino acid, the polypeptide having epidermal growth factor receptor antagonist activity.

3. The epidermal growth factor polypeptide variant of claim 2, wherein the amino acid substitution at the position that corresponds to Gly 18 or Gly 39 of human wild-type epidermal growth factor is selected from the group consisting of: phenylalanine, leucine, aspartic acid, and isoleucine.

4. The epidermal growth factor polypeptide variant of claim 1, wherein the amino acid corresponding to Val 35 of human wild-type epidermal growth factor is substituted with glutamate.

5. The epidermal growth factor polypeptide variant of claim 2, wherein Gly 18 or Gly 39 is substituted.

6. The epidermal growth factor polypeptide variant of claim 2, wherein Val 35 is substituted with glutamate.

7. The epidermal growth factor polypeptide variant of claim 2, wherein the amino acid substitution is a conservative amino acid substitution.

8. The epidermal growth factor polypeptide variant of claim 2, wherein Gly 18 and Gly 39 is substituted.

9. The epidermal growth factor polypeptide variant of human EGF in which the amino acid position that corresponds to amino acid Val 35 is substituted with glutamate and the amino acid Gly 39 is substituted with leucine.

10. A composition comprising the EGFR ligand polypeptide variant of claim 1 and a pharmaceutically acceptable carrier.

11. A polypeptide variant of an epidermal growth factor receptor ligand, the ligand being selected from the group consisting of transforming growth factor-α (TGFα), betacellulin, heparin-binding EGF-like growth factor (HB-EGF), amphiregulin (AR) and epiregulin, in which the amino acid position that corresponds to amino acid Gly 18 or amino acid Gly 39 of human wild-type epidermal growth factor is substituted with another amino acid, the polypeptide having epidermal growth factor receptor antagonist activity.

* * * * *

SEQUENCE LISTING

```
<160> NUMBER OF SEQ ID NOS: 12

<210> SEQ ID NO 1
<211> LENGTH: 53
<212> TYPE: PRT
<213> ORGANISM: Homo Sapien

<400> SEQUENCE: 1

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg
    50

<210> SEQ ID NO 2
<211> LENGTH: 53
<212> TYPE: PRT
<213> ORGANISM: Pig
```

-continued

<400> SEQUENCE: 2

Asn Ser Tyr Ser Glu Cys Pro Pro Ser His Asp Gly Tyr Cys Leu His
1               5                   10                  15

Gly Gly Val Cys Met Tyr Ile Glu Ala Val Asp Ser Tyr Ala Cys Asn
            20                  25                  30

Cys Val Phe Gly Tyr Val Gly Glu Arg Cys Gln His Arg Asp Leu Lys
        35                  40                  45

Trp Trp Glu Leu Arg
    50

<210> SEQ ID NO 3
<211> LENGTH: 52
<212> TYPE: PRT
<213> ORGANISM: Cat

<400> SEQUENCE: 3

Asn Ser Tyr Gln Glu Cys Pro Pro Ser Tyr Asp Gly Tyr Cys Leu Tyr
1               5                   10                  15

Asn Gly Val Cys Met Tyr Ile Glu Ala Val Asp Arg Tyr Ala Cys Asn
            20                  25                  30

Cys Val Phe Gly Tyr Val Gly Glu Arg Cys Gln His Arg Asp Leu Lys
        35                  40                  45

Trp Glu Leu Arg
    50

<210> SEQ ID NO 4
<211> LENGTH: 52
<212> TYPE: PRT
<213> ORGANISM: Dog

<400> SEQUENCE: 4

Asn Gly Tyr Arg Glu Cys Pro Ser Ser Tyr Asp Gly Tyr Cys Leu Tyr
1               5                   10                  15

Asn Gly Val Cys Met Tyr Ile Glu Ala Val Asp Arg Tyr Ala Cys Asn
            20                  25                  30

Cys Val Phe Gly Tyr Val Gly Glu Arg Cys Gln His Arg Asp Leu Lys
        35                  40                  45

Trp Glu Leu Arg
    50

<210> SEQ ID NO 5
<211> LENGTH: 53
<212> TYPE: PRT
<213> ORGANISM: Mouse

<400> SEQUENCE: 5

Asn Ser Tyr Pro Gly Cys Pro Ser Ser Tyr Asp Gly Tyr Cys Leu Asn
1               5                   10                  15

Gly Gly Val Cys Met His Ile Glu Ser Leu Asp Ser Tyr Thr Cys Asn
            20                  25                  30

Cys Val Ile Gly Tyr Ser Gly Asp Arg Cys Gln Thr Arg Asp Leu Arg
        35                  40                  45

Trp Trp Glu Leu Arg
    50

<210> SEQ ID NO 6
<211> LENGTH: 48
<212> TYPE: PRT
<213> ORGANISM: Horse

<400> SEQUENCE: 6

Asn Ser Tyr Gln Glu Cys Ser Gln Ser Tyr Asp Gly Tyr Cys Leu His
1               5                   10                  15
Gly Gly Lys Cys Val Tyr Leu Val Gln Val Asp Thr His Ala Cys Asn
            20                  25                  30
Cys Val Val Gly Tyr Val Gly Glu Arg Cys Gln His Gln Asp Leu Arg
        35                  40                  45

<210> SEQ ID NO 7
<211> LENGTH: 53
<212> TYPE: PRT
<213> ORGANISM: Rat

<400> SEQUENCE: 7

Asn Ser Asn Thr Gly Cys Pro Pro Ser Tyr Asp Gly Tyr Cys Leu Asn
1               5                   10                  15
Gly Gly Val Cys Met Tyr Val Glu Ser Val Asp Arg Tyr Val Cys Asn
            20                  25                  30
Cys Val Ile Gly Tyr Ile Gly Glu Arg Cys Gln His Arg Asp Leu Arg
        35                  40                  45
Trp Trp Lys Leu Arg
    50

<210> SEQ ID NO 8
<211> LENGTH: 50
<212> TYPE: PRT
<213> ORGANISM: Artificial Sequence
<220> FEATURE:
<223> OTHER INFORMATION: Syntheic

<400> SEQUENCE: 8

Val Val Ser His Phe Asn Asp Cys Pro Asp Ser His Thr Gln Phe Cys
1               5                   10                  15
Phe His Gly Thr Cys Arg Phe Leu Val Gln Glu Asp Lys Pro Ala Cys
            20                  25                  30
Val Cys His Ser Gly Tyr Val Gly Ala Arg Cys Glu His Ala Asp Leu
        35                  40                  45
Leu Ala
    50

<210> SEQ ID NO 9
<211> LENGTH: 118
<212> TYPE: PRT
<213> ORGANISM: Aftifical Sequence
<220> FEATURE:
<223> OTHER INFORMATION: Synthetic

<400> SEQUENCE: 9

Met Thr Ala Gly Arg Arg Met Glu Met Leu Cys Ala Gly Arg Val Pro
1               5                   10                  15
Ala Leu Leu Leu Cys Leu Gly Phe His Leu Leu Gln Ala Val Leu Ser
            20                  25                  30
Thr Thr Val Ile Pro Ser Cys Ile Pro Gly Ser Ser Asp Asn Cys Thr
        35                  40                  45
Ala Leu Val Gln Thr Glu Asp Asn Pro Arg Val Ala Gln Val Ser Ile
    50                  55                  60
Thr Lys Cys Ser Ser Asp Met Asn Gly Tyr Cys Leu His Gly Gln Cys
65                  70                  75                  80

-continued

Ile Tyr Leu Val Asp Met Ser Gln Asn Tyr Cys Arg Cys Glu Val Gly
                85                  90                  95

Tyr Thr Gly Val Arg Cys Glu His Phe Phe Leu Thr Val His Gln Pro
            100                 105                 110

Leu Ser Lys Glu Tyr Val
        115

<210> SEQ ID NO 10
<211> LENGTH: 123
<212> TYPE: PRT
<213> ORGANISM: Artificial Sequence
<220> FEATURE:
<223> OTHER INFORMATION: Synthetic

<400> SEQUENCE: 10

Met Asp Arg Ala Ala Arg Cys Ser Gly Ala Ser Ser Leu Pro Leu Leu
  1               5                  10                  15

Leu Ala Leu Ala Leu Gly Leu Val Ile Leu His Cys Val Val Ala Asp
                20                  25                  30

Gly Asn Ser Thr Arg Ser Pro Glu Thr Asn Gly Leu Leu Cys Gly Asp
            35                  40                  45

Pro Glu Glu Asn Cys Ala Ala Thr Thr Thr Gln Ser Lys Arg Lys Gly
        50                  55                  60

His Phe Ser Arg Cys Pro Lys Gln Tyr Lys His Tyr Cys Ile Lys Gly
 65                 70                  75                  80

Arg Cys Arg Phe Val Val Ala Glu Gln Thr Pro Ser Cys Val Cys Asp
                85                  90                  95

Glu Gly Tyr Ile Gly Ala Arg Cys Glu Arg Val Asp Leu Phe Tyr Leu
            100                 105                 110

Arg Gly Asp Arg Gly Gln Ile Leu Val Ile Cys
        115                 120

<210> SEQ ID NO 11
<211> LENGTH: 252
<212> TYPE: PRT
<213> ORGANISM: Artificial Sequence
<220> FEATURE:
<223> OTHER INFORMATION: Synthetic

<400> SEQUENCE: 11

Met Arg Ala Pro Leu Leu Pro Pro Ala Pro Val Val Leu Ser Leu Leu
  1               5                  10                  15

Ile Leu Gly Ser Gly His Tyr Ala Ala Gly Leu Asp Leu Asn Asp Thr
                20                  25                  30

Tyr Ser Gly Lys Arg Glu Pro Phe Ser Gly Asp His Ser Ala Asp Gly
            35                  40                  45

Phe Glu Val Thr Ser Arg Ser Glu Met Ser Ser Gly Ser Glu Ile Ser
        50                  55                  60

Pro Val Ser Glu Met Pro Ser Ser Ser Glu Pro Ser Ser Gly Ala Asp
 65                 70                  75                  80

Tyr Asp Tyr Ser Glu Glu Tyr Asp Asn Glu Pro Gln Ile Pro Gly Tyr
                85                  90                  95

Ile Val Asp Asp Ser Val Arg Val Glu Gln Val Val Lys Pro Pro Gln
            100                 105                 110

Asn Lys Thr Glu Ser Glu Asn Thr Ser Asp Lys Pro Lys Arg Lys Lys
        115                 120                 125

Lys Gly Gly Lys Asn Gly Lys Asn Arg Arg Asn Arg Lys Lys Lys Asn
        130                 135                 140

```
Pro Cys Asn Ala Glu Phe Gln Asn Phe Cys Ile His Gly Glu Cys Lys
145                 150                 155                 160

Tyr Ile Glu His Leu Glu Ala Val Thr Cys Lys Cys Gln Gln Glu Tyr
                165                 170                 175

Phe Gly Glu Arg Cys Gly Glu Lys Ser Met Lys Thr His Ser Met Ile
            180                 185                 190

Asp Ser Ser Leu Ser Lys Ile Ala Leu Ala Ala Ile Ala Ala Phe Met
        195                 200                 205

Ser Ala Val Ile Leu Thr Ala Val Ala Val Ile Thr Val Gln Leu Arg
    210                 215                 220

Arg Gln Tyr Val Arg Lys Tyr Glu Gly Glu Ala Glu Glu Arg Lys Lys
225                 230                 235                 240

Leu Arg Gln Glu Asn Gly Asn Val His Ala Ile Ala
                245                 250
```

<210> SEQ ID NO 12
<211> LENGTH: 208
<212> TYPE: PRT
<213> ORGANISM: Artificial Sequence
<220> FEATURE:
<223> OTHER INFORMATION: Synthetic

<400> SEQUENCE: 12

```
Met Lys Leu Leu Pro Ser Val Val Leu Lys Leu Phe Leu Ala Ala Val
1               5                   10                  15

Leu Ser Ala Leu Val Thr Gly Glu Ser Leu Glu Arg Leu Arg Arg Gly
            20                  25                  30

Leu Ala Ala Gly Thr Ser Asn Pro Asp Pro Thr Val Ser Thr Asp
        35                  40                  45

Gln Leu Leu Pro Leu Gly Gly Gly Arg Asp Arg Lys Val Arg Asp Leu
    50                  55                  60

Gln Glu Ala Asp Leu Asp Leu Leu Arg Val Thr Leu Ser Ser Lys Pro
65                  70                  75                  80

Gln Ala Leu Ala Thr Pro Asn Lys Glu Glu His Gly Lys Arg Lys Lys
                85                  90                  95

Lys Gly Lys Gly Leu Gly Lys Lys Arg Asp Pro Cys Leu Arg Lys Tyr
            100                 105                 110

Lys Asp Phe Cys Ile His Gly Glu Cys Lys Tyr Val Lys Glu Leu Arg
        115                 120                 125

Ala Pro Ser Cys Ile Cys His Pro Gly Tyr His Gly Glu Arg Cys His
    130                 135                 140

Gly Leu Ser Leu Pro Val Glu Asn Arg Leu Tyr Thr Tyr Asp His Thr
145                 150                 155                 160

Thr Ile Leu Ala Val Val Ala Val Val Leu Ser Ser Val Cys Leu Leu
                165                 170                 175

Val Ile Val Gly Leu Leu Met Phe Arg Tyr His Arg Arg Gly Gly Tyr
            180                 185                 190

Asp Val Glu Asn Glu Glu Lys Val Lys Leu Gly Met Thr Asn Ser His
        195                 200                 205
```